(12) United States Patent
Baratta et al.

(10) Patent No.: US 11,577,233 B2
(45) Date of Patent: Feb. 14, 2023

(54) MONOCARBONYL RUTHENIUM AND OSMIUM CATALYSTS

(71) Applicants: UNIVERSITA DEGLI STUDI DI UDINE, Udine (IT); INNOVATION FACTORY S.R.L., Trieste (IT)

(72) Inventors: Walter Baratta, Udine (IT); Salvatore Baldino, Sassari (IT); Steven Giboulot, Sainte-Maxime (FR)

(73) Assignees: Universita' Delgi Studi Di Udine, Udine (IT); Innovation Factory S.R.L., Trieste (IT)

(*) Notice: Subject to any disclaimer, the term of this patent is extended or adjusted under 35 U.S.C. 154(b) by 0 days.

(21) Appl. No.: 17/673,220

(22) Filed: Feb. 16, 2022

(65) Prior Publication Data

US 2022/0168720 A1 Jun. 2, 2022

Related U.S. Application Data

(62) Division of application No. 16/075,315, filed as application No. PCT/IB2017/050598 on Feb. 3, 2017, now Pat. No. 11,278,876.

(30) Foreign Application Priority Data

Feb. 5, 2016 (IT) .................... 102016000011905

(51) Int. Cl.
| | |
|---|---|
| *B01J 31/24* | (2006.01) |
| *C07B 41/02* | (2006.01) |
| *C07F 15/00* | (2006.01) |
| *C07C 29/143* | (2006.01) |
| *C07C 29/145* | (2006.01) |
| *C07C 41/26* | (2006.01) |
| *C07C 201/12* | (2006.01) |
| *C07C 29/14* | (2006.01) |
| *B01J 31/18* | (2006.01) |

(52) U.S. Cl.
CPC ......... *B01J 31/2452* (2013.01); *B01J 31/182* (2013.01); *B01J 31/189* (2013.01); *B01J 31/2433* (2013.01); *C07B 41/02* (2013.01); *C07C 29/14* (2013.01); *C07C 29/143* (2013.01); *C07C 29/145* (2013.01); *C07C 41/26* (2013.01); *C07C 201/12* (2013.01); *C07F 15/0053* (2013.01); *B01J 2231/641* (2013.01); *B01J 2531/0244* (2013.01); *B01J 2531/821* (2013.01); *B01J 2531/825* (2013.01); *C07C 2602/10* (2017.05)

(58) Field of Classification Search
None
See application file for complete search history.

(56) References Cited

FOREIGN PATENT DOCUMENTS

| | | |
|---|---|---|
| EP | 0773064 A1 | 5/1997 |
| JP | H07500630 A | 1/1995 |
| JP | H09262477 A | 10/1997 |
| WO | 9404497 A1 | 3/1994 |
| WO | 2005051965 A2 | 6/2005 |
| WO | 2009007443 A2 | 1/2009 |
| WO | 2011048727 A1 | 4/2011 |
| WO | 2012123761 A1 | 9/2012 |

OTHER PUBLICATIONS

Liu et al. Chem. Eur. J., 16, 7889-7897 (Year: 2010).*
Aguirre et al., Applied Organometallic Chemistry, 2002, 16: pp. 597-600.
Moreno et al., Journal of Organometallic Chemistry, 690, 2005, pp. 3803-3814.
John et al., Chem.Ber, 103, 1970, pp. 2178-2196.
Popov, A., Zhumal Obschchei Khimii, vol. 58, Issue 5, 1988, pp. 1172-1173.
Kumar et al., Inorganica Chimica Acta, 368, 2011, pp. 124-131.
Chelucci et al., Coordination Chemistry Reviews, 300, 2015, pp. 29-85.
Spiccia et al., Coordination Chemistry Reviews, 284, 2004, pp. 1329-1341.
Joshi et al., ChemMedChem, 9, 2014, pp. 1419-1427.
Kamatchi et al., European Journal of Medicinal Chemistry, 59, 2013, pp. 253-264.
Baratta et al, Agnew. Chem. Int., ed, 2004, 43, pp. 3584-3588.
Baratta et al., Organometallics 2004, 23, pp. 6264-6272.
Bera et al., International Journal for Inorganic, Organometallic and Bioinorganic Chemistry, vol. 43, No. 12, Jan. 1, 2014, pp. 4726-4733.
Cavarzan et al., Polyhedron, vol. 62, Oct. 7, 2013, pp. 75-82.
Cavarzan et al., Transition Metal Chemistry, vol. 40, No. 1, Oct. 31, 2014, pp. 117-123.
Jung et al., Bull. Korean. Chem. Soc. 1997, vol. 18, No. 8, pp. 806-810.
Mezzeiti et al., Gazzetta Chmiica Italiana, 123, 1993, pp. 155-164.
Zhang, et al., Organometallics 2013, 32, pp. 5299-5304.

\* cited by examiner

*Primary Examiner* — Yun Qian
(74) *Attorney, Agent, or Firm* — BakerHostetler

(57) ABSTRACT

The invention relates to monocarbonyl complexes of ruthenium and osmium with bi- and tridentate nitrogen and phosphine ligands. The invention relates to methods for preparing these complexes and the use of these complexes, isolated or prepared in situ, as catalysts for reduction reactions of ketones and aldehydes both via transfer hydrogenation or hydrogenation with hydrogen.

9 Claims, No Drawings

MONOCARBONYL RUTHENIUM AND OSMIUM CATALYSTS

CROSS-REFERENCE TO RELATED APPLICATIONS

This application is a divisional of U.S. patent application Ser. No. 16/075,315, filed Aug. 3, 2018, which is a U.S. national stage of International Patent Application No. PCT/IB2017/050598, filed Feb. 3, 2017, which claims priority of Italian Patent Application No. 102016000011905, filed Feb. 5, 2016, the disclosures of which are incorporated by reference herein.

DESCRIPTION

The invention relates to monocarbonyl complexes of ruthenium and osmium with bi- and tridentate nitrogen and phosphine ligands. The invention relates to methods for preparing these complexes and the use of these complexes, isolated or prepared in situ, as catalysts for reduction reactions of ketones and aldehydes both via transfer hydrogenation or hydrogenation with hydrogen.

STATE OF THE ART

The carbonyl compounds (aldehydes and ketones) can be easily reduced to alcohols by molecular hydrogen (hydrogenation) or hydrogen donor molecules (transfer hydrogenation) through the use of catalysts based on rhodium, iridium, iron, ruthenium and osmium.

The development of complexes that catalyze the chemo- and stereo-selective reduction of carbonyl compounds is a subject of considerable academic and industrial interest, a target which can be achieved through the fine-tuning of the ligands of the complexes.

The hydrogenation, which entails the use of hydrogen under pressure, is an industrial process for the synthesis of alcohols. A significant breakthrough for the development and application of this process was given in the late '90s by a new class of ruthenium complexes of formula $RuCl_2(P)_2$(diamine) and $RuCl_2(PP)$(diamine) (P=phosphine and PP=diphosphine) for the catalytic enantioselective hydrogenation of ketones. By using a suitable combination of chiral diphosphine and diamine ligands, these complexes were proven to efficiently catalyze the asymmetric reductions of carbonyl compounds with production of chiral alcohols with high enantiomeric excess.

In addition to hydrogenation, the transfer hydrogenation reaction has also been developed using 2-propanol or formic acid as hydrogen source, with the advantage of employing non-pressure systems and reducing the risk.

In 2004 Baratta and collaborators have developed ruthenium complexes containing phosphines and bi- and tridentate aminopyridine ligands which show high catalytic activity in hydrogenation and transfer hydrogenation reactions.

Recently, the complexes trans-$RuCl_2(CO)(NN)(PR_3)$ (R=Ph, p-tolyl; NN=ethylenediamine, 2-aminomethylpyridine and bipyridine) were isolated and they were found active in the transfer hydrogenation of ketones (D. A. Cavarzan et al., *Polyhedron* 2013, 62, 75). It is worth noting that the carbonyl complexes $[RuX(CO)(NN)(PP)]Cl$ (X=Cl, H, NN=ethylenediamine or 2-aminomethylpyridine) and $RuCl(CP)(CO)(NN)$ containing a cyclometallated phosphine (CP) isolated by Baratta and co-workers display high catalytic activity in the transfer hydrogenation of ketones (S. Zhang et al., *Organometallics* 2013, 32, 5299; W. Baratta et al., *Angew. Chem. Int. Ed.* 2004, 43, 3584; W. Baratta et al., *Organometallics* 2004, 23, 6264 and WO2005/051965). Complexes of the formula $RuCl_2(CO)(dmf)(PP)$ have been found active in hydrogenation, transfer hydrogenation, hydroformylation and carbonylation reactions (WO2012/123761 A1).

The interest in these systems stems from the fact that the presence of a Ru—CO bond makes the catalyst more robust and less sensitive to the decarbonylation reactions of the substrates which can deactivate the catalysts, preventing their use in very low quantities.

Moreover, to make the reduction of carbonyl compounds to alcohols economically competitive, via transfer hydrogenation or hydrogenation, the development of catalysts with high chemo- and stereoselectivity is a crucial issue. Furthermore, the catalysts have to display high productivity and should be easily prepared from commercially available starting material through simple and safe synthetic routes.

The purpose of the present invention relates to the synthesis of complexes of ruthenium and osmium containing a CO ligand in combination with bidentate and tridentate nitrogen ligands and achiral or chiral phosphines. These complexes can be used as catalysts in the (asymmetric) reduction of carbonyl compounds by transfer hydrogenation or hydrogenation with molecular hydrogen.

A further object of the present invention is to obtain ruthenium (II) and osmium (II) complexes which can be generated in situ during the reduction of carbonyl compounds or by transfer hydrogenation or hydrogenation with molecular hydrogen.

SUMMARY OF THE INVENTION

In order to achieve the purposes mentioned above the inventors have identified in a series of monocarbonyl complexes of ruthenium and osmium, containing nitrogen and phosphine ligands, the solution for obtaining catalysts with high catalytic activity in hydrogenation reactions with molecular hydrogen and transfer hydrogenation of carbonyl compounds to alcohols.

Accordingly, the present disclosure refers to a pentacoordinate or hexacoordinate complex of formula (1):

  (1)

wherein
M=Ru or Os;
a, b and d are independently 0 or 1;
c is 1 or 2;
X, Y are independently selected among halides, hydride, C1-C20 carboxylates and C1-C20 alkoxides;
W is selected among halides, C1-C20 carboxylates and C1-C20 alkoxides;
L is a nitrogen-containing ligand selected among:
(I) a NN compound of formula Ia to Ic:

  (Ia)

  (Ib)

-continued

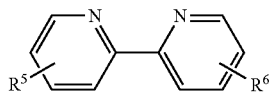
(Ic)

(II) a HCNN compound of formula IIa-IIb and a CNN ligand of formula IIc-IId:

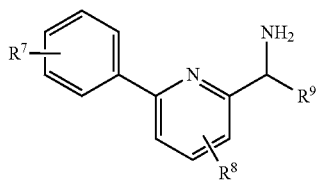
(IIa)

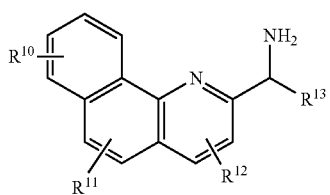
(IIb)

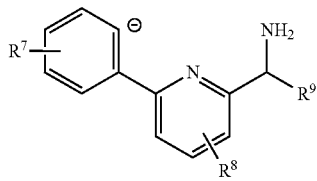
(IIc)

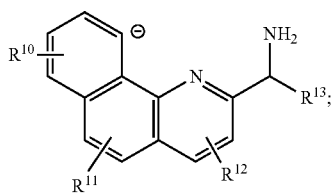
(IId)

(III) a HCN compound of formula IIIa

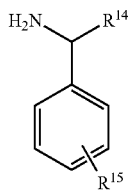
(IIIa)

wherein
$R^1$-$R^{15}$ are independently selected among H, C1-C20 aliphatic groups and C5-C20 aromatic groups;

L' is at least one phosphorus-containing ligand selected among:

a phosphine (P) selected among: a phosphine of formula $PR^{16}R^{17}R^{18}$, wherein $R^{16}$-$R^{18}$ are independently selected among H, C1-C20 aliphatic groups and C5-C20 aromatic groups; an optically active phosphine selected among (S)-neomenthyldiphenylphosphine and (R)-(+)-2-(diphenylphosphino)-2'-methoxy-1,1'-binaphthyl, a diphosphine (PP) selected among: a diphosphine of formula $P(R^{19})_2$—Z—$P(R^{20})_2$, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups; an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane, a HCP compound of formula (IVa) and a CP ligand of formula (IVb)

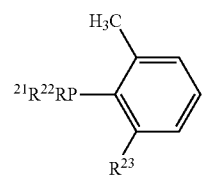
(IVa)

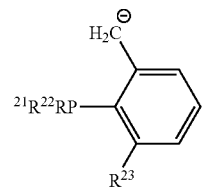
(IVb)

a PNN compound of formula (V)

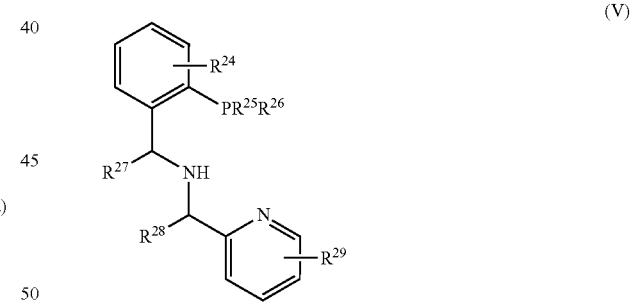
(V)

wherein
$R^{21}$-$R^{29}$ are independently selected among H, C1-C20 aliphatic groups and C5-C20 aromatic groups;

provided that:
when a=b=c=1; d=0; X=Y=Cl; L is ethylenediamine or 2-(aminomethyl)pyridine or 2,2'-bipyridine or 4,4'-dimethyl-2,2'-bipyridine, L' is not a phosphine (P) of formula $PR^{16}R^{17}R^{18}$ in which $R^{16}$=$R^{17}$=$R^{18}$=phenyl or p-tolyl, when a=0; b=c=d=1; X=W=Cl or X=H and W=Cl, L=ethylenediamine or 2-(aminomethyl)pyridine, L' is not $Ph_2P(CH_2CH_2CH_2)PPh_2$;

when a=d=0; b=c=1; X=Cl; L=ethylenediamine or 2-(aminomethyl)pyridine, L' is not a ligand (CP) of formula (IVb) in which $R^{21}$=$R^{22}$=phenyl and $R^{23}$=methyl; and when a, b and d are 0, c is 2, X is Cl and $R^{23}$ is —$CH_3$, $R^{21}$ and $R^{22}$ are not phenyl groups.

In a further aspect, the present disclosure refers to the use of said ruthenium or osmium complexes as catalyst or pre-catalyst for the reduction reaction of ketones or aldehydes to alcohols by transfer hydrogenation or hydrogenation with molecular hydrogen.

This and other aspects as well as the characteristics and advantages of the present invention will be more apparent from the detailed description below and by the preferred embodiments given as non-limiting illustrations of the invention itself.

DESCRIPTION OF THE INVENTION

As used therein, "aliphatic group" refers to acyclic or cyclic, linear or branched, saturated or unsaturated hydrocarbons, excluding aromatic groups.

As used therein, "substituted aliphatic group" refers to an aliphatic group in which at least one hydrogen atom is replaced by at least one substituent group selected among —OR', —NRR', —NRCOR', —$NO_2$, —$NH_2$, —COR, —COOR, —CONRR' and halides, wherein R and R' are equal or different and can be a H or a C1-C20 aliphatic or aromatic group.

As used therein, "aromatic group" also include aromatic compounds substituted with aliphatic groups.

As used therein, "substituted aromatic group" refers to an aromatic group in which at least one aromatic hydrogen atom is replaced with at least one substituent group selected among —R, —OR, —NRR', —NRCOR', —$NO_2$, —$NH_2$, —COR, —COOR, —CONRR' and halides, wherein R and R' are equal or different and can be a H or a C1-C20 aliphatic or aromatic group.

As used therein, "heteroaromatic group" refers to aromatic groups in which at least one carbon atom which is part of the aromatic ring is replaced with one heteroatom selected among N, S, O and P.

As used therein, "hydrogen-donor" refers to a compound that transfers a hydrogen atom to another compound.

As used therein, "(transfer)hydrogenation" refers to hydrogenation with molecular hydrogen or to transfer hydrogenation using a hydrogen donor compound.

In the present description and appended claims the abbreviations listed in Table 1 are used:

TABLE 1

Abbreviation of the nitrogen and phosphorus ligands

| Chemical name | Abbreviation | Structural formula |
|---|---|---|
| Nitrogen-containing ligand L | | |
| ethylenediamine | en | |
| 2-(aminomethyl)pyridine | ampy | |
| bipyridine | bipy | |

TABLE 1-continued

Abbreviation of the nitrogen and phosphorus ligands

| Chemical name | Abbreviation | Structural formula |
|---|---|---|
| (1R,2R)-1,2-diphenylethylenediamine | (R,R)-dpen | |
| (1S,2S)-1,2-diphenylethylenediamine | (S,S)-dpen | |
| 6-(4-methylphenyl)-2-(aminomethyl)pyridine | Hamtp | |
| Anionic form of 6-(4-methylphenyl)-2-(aminomethyl)pyridine | amtp | |
| 2-(aminomethyl)benzo[h]quinoline | Hambq | |
| Anionic form of 2-(aminomethyl)benzo[h]quinoline | ambq | |
| 4-phenyl-2-(aminomethyl)benzo[h]quinoline | Hambq$^{Ph}$ | |
| Anionic form of 4-phenyl-2-(aminomethyl)benzo[h]quinoline | ambq$^{Ph}$ | |
| benzylamine | HCN | |

TABLE 1-continued

Abbreviation of the nitrogen and phosphorus ligands

| Chemical name | Abbreviation | Structural formula |
|---|---|---|
| Anionic form of benzylamine | CN | | phosphorus-containing ligand L'

| Chemical name | Abbreviation |
|---|---|
| triphenylphosphine | $PPh_3$ |
| tricyclohexylphosphine | $PCy_3$ |
| triisopropylphosphine | $PiPr_3$ |
| 1,3-bis(diphenylphosphino)propane | dppp |
| 1,4-bis(diphenylphosphino)butane | dppb |
| 1,1'-bis(diphenylphosphino)ferrocene | dppf |
| (R)-1-[($S_P$)-2-(diphenylphosphino)ferrocenylethyl]diphenylphosphine | (R)-Josiphos |
| (R)-(+)-2,2'-bis(diphenylphosphino)-1,1'-binaphthalene | (R)-BINAP |
| (R,R)-Skewphos | (R,R)-BDPP |
| (2,6-dimethylphenyl)diphenylphosphine | Hdmpp |
| Anionic form of (2,6-dimethylphenyl)diphenylphosphine | dmpp |
| (2,6-dimethylphenyl)dicyclohexylphosphine | Hdmppc |
| Anionic form of (2,6-dimethylphenyl)dicyclohexylphosphine | dmppc |
| | PNN |

The present disclosure refers to a pentacoordinate or hexacoordinate complex of formula (1):

$$[MXY_a(CO)L_bL'_c]W_d \qquad (1)$$

wherein
M=Ru or Os;
a, b and d are independently 0 or 1;
cis 1 or 2;
X, Y are independently selected among halides, hydride, C1-C20 carboxylates and C1-C20 alkoxides;
W is selected among halides, C1-C20 carboxylates and C1-C20 alkoxides;
L is a nitrogen-containing ligand selected among:
(I) a NN compound of formula Ia to Ic:

(Ia)

(Ib)

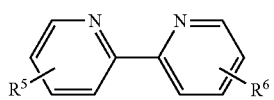
(Ic)

(II) a HCNN compound of formula IIa-IIb and a CNN ligand of formula IIc-IId:

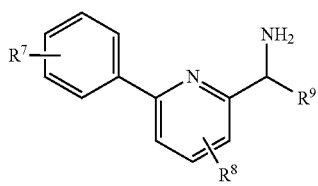
(IIa)

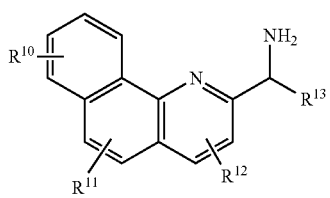
(IIb)

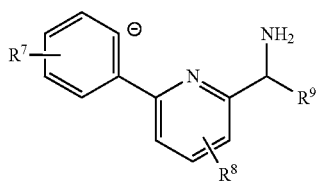
(IIc)

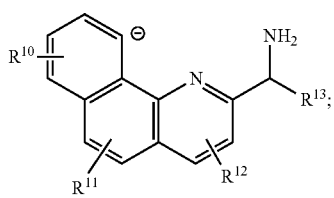
(IId)

(III) a HCN compound of formula IIIa

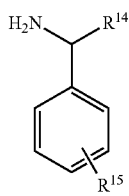
(IIIa)

wherein
$R^1$-$R^{15}$ are independently selected among H, C1-C20 aliphatic groups and C5-C20 aromatic groups, preferably $R^1$ and $R^2$ may be independently selected among H and a phenyl group and/or $R^3$-$R^6$ and $R^8$-$R^{15}$ may be H and/or $R^7$ may be 4-methyl;

L' is at least one phosphorus-containing ligand selected among:
a phosphine (P) selected among: a phosphine of formula $PR^{16}R^{17}R^{18}$, wherein $R^{16}$-$R^{18}$ are independently selected among H, C1-C20 aliphatic groups and C5-C20 aromatic groups; an optically active phosphine selected among (S)-neomenthyldiphenylphosphine and (R)-(+)-2-(diphenylphosphino)-2'-methoxy-1,1'-binaphthyl, a diphosphine (PP) selected among: a diphosphine of formula $P(R^{19})_2$—Z—$P(R^{20})_2$, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups; an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane, a HCP compound of formula (IVa) and a CP ligand of formula (IVb)

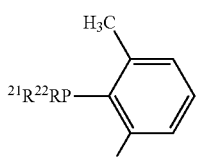
(IVa)

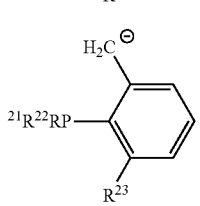
(IVb)

wherein
$R^{21}$-$R^{23}$ are independently selected among H, C1-C20 aliphatic groups and C5-C20 aromatic groups, preferably $R^{23}$ may be —$CH_3$ and/or $R^{21}$-$R^{22}$ may be C6-C20 cycloaliphatic group or C6-C20 aromatic group, more preferably $R^{23}$ may be —$CH_3$ and/or $R^{21}$-$R^{22}$ may be independently selected among phenyl and cyclohexyl group a PNN compound of formula (V)

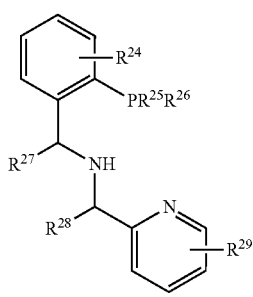
(V)

wherein
$R^{24}$-$R^{29}$ are independently selected among H, C1-C20 aliphatic groups and C5-C20 aromatic groups, preferably $R^{24}$ and $R^{27}$-$R^{29}$ may be H and/or $R^{25}$ and $R^{26}$ may be a C1-C20 aromatic group, more preferably a phenyl group;

provided that:
when a=b=c=1; d=0; X=Y=Cl, L is ethylenediamine or 2-(aminomethyl)pyridine or 2,2'-bipyridine or 4,4'-dimethyl-2,2'-bipyridine, L' is not a phosphine (P) of formula $PR^{16}R^{17}R^{18}$ in which $R^{16}=R^{17}=R^{18}$=phenyl or p-tolyl,
when a=0; b=c=d=1; X=W=Cl or X=H and W=Cl, L=ethylenediamine or 2-(aminomethyl)pyridine, L' is not $Ph_2P(CH_2CH_2CH_2)PPh_2$;
when a=d=0; b=c=1; X=Cl; L=ethylenediamine or 2-(aminomethyl)pyridine, L' is not a ligand (CP) of formula (IVb) in which $R^{21}=R^{22}$=phenyl and $R^{23}$=methyl; and
when a, b and d are 0, c is 2, X is Cl and $R^{23}$ is —$CH_3$, $R^{21}$ and $R^{22}$ are not phenyl groups.

In complexes of formula (1), when c=2 and L' represents two phosphorus-containing ligands independently selected among the phosphorus-containing compounds listed above, when one L' is CP and one L' is HCP, the complex of formula (1) is pentacoordinate complex.

The high modularity of the nitrogen-containing ligands (Ia-c), (IIa-d) and (IIIa) in combination with phosphines (P), diphosphines (PP), HCP phosphines and PNN phosphines, allows to obtain a large number of well-defined catalysts displaying high chemo- and stereoselectivity.

For the purposes of the present invention, from the combination of the different meanings of X, Y, W, L, and L', the complexes of sub-formulas (VI-XIV) given below may be obtained, which are encompassed by the general formula (1).

According to an embodiment, the bidentate (NN) ligands of type (Ia-c) have the ability, through the nitrogen atoms of a —$NH_2$ group or of a heterocycle in combination with monodentate phosphines, to coordinate the metal. Thus, the present disclosure may refer to a complex of formula (VI)

MXY(CO)(NN)(P)  (VI)

wherein M, X, Y, (NN) and (P) are as defined above, provided that when X and Y are Cl, $R^{16}$-$R^{18}$ are not phenyl or p-tolyl groups.

According to a specific embodiment, the present disclosure may refer to complexes of formula (VI) wherein M, X, Y, (NN) and (P) are as defined above, provided that when X and Y are Cl, $R^{16}$-$R^{18}$ are not aromatic groups.

Complexes of formula (VI) can be obtained as a mixture of trans-isomers (e.g. complex 4 and 6 below) and cis-isomers (e.g. complex 5 and 7).

The present disclosure also refers to a process to obtain complexes of formula (VI) comprising reacting a compound of formula $MXY(CO)(PPh_3)_2$, or of formula $MXY(CO)(PPh_3)_2(dmf)$, wherein M, X, Y are as defined above and (dmf) is dimethylformamide, with a phosphine (P) selected among:
phosphines of formula $PR^{16}R^{17}R^{18}$, wherein $R^{16}$-$R^{18}$ are independently selected among H, C1-C20 aliphatic group and C5-C20 aromatic groups; and
an optically active phosphine selected among (S)-neomenthyldiphenylphosphine and (R)-(+)-2-(diphenylphosphino)-2'-methoxy-1,1'-binaphthyl;
and at least one nitrogen-containing compound NN selected among

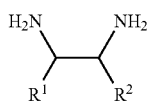

(Ia)

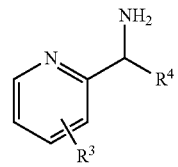

(Ib)

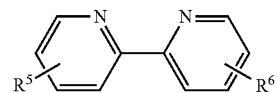

(Ic)

wherein
$R^1$-$R^6$ are independently selected among H, C1-C20 aliphatic group and C5-C20 aromatic group, preferably $R^1$ and $R^2$ may be independently selected among H and a phenyl group and/or $R^3$-$R^6$ may be H. Compounds of formula $MXY(CO)(PPh_3)_2$ or of formula $MXY(CO)(PPh_3)_2(dmf)$ may be prepared by reacting compounds of formula $MXY(PPh_3)_k$, wherein k is 2 or 3 with carbon monoxide, in the presence of a suitable organic solvent and optionally of dimethylformamide.

According to an embodiment, when X=Y=Cl, the compound $MCl_2(CO)(PPh_3)_2(dmf)$ may be formed by reacting $MCl_2(PPh_3)_3$ with CO in the presence of dimethylformamide and a suitable organic solvent. When M is Ru, the compound $RuCl_2(CO)(PPh_3)_2(dmf)$ may be formed by reacting $RuCl_2(PPh_3)_3$ with CO in the presence of dimethylformamide and a suitable organic solvent.

According to an embodiment, when X=Y=acetate (OAc), the compound $M(OAc)_2(CO)(PPh_3)_2$ may be formed by reacting $M(OAc)_2(PPh_3)_2$ with CO in the presence of a suitable organic solvent. When M is Ru, the compound $Ru(OAc)_2(CO)(PPh_3)_2$ may be formed by reacting $Ru(OAc)_2 (PPh_3)_2$ with CO in the presence of a suitable organic solvent.

Compounds such as $RuCl_2(PPh_3)_3$ and $Ru(OAc)_2(PPh_3)_2$ are commercially available.

According to a preferred embodiment, the present disclosure may refer to a process to obtain a complex of formula (VI) wherein M is Ru and X=Y=Cl or acetate (OAc), by reacting $RuCl_2(CO)(PPh_3)_2(dmf)$ or $Ru(OAc)_2(CO)(PPh_3)_2$ with a phosphine (P) selected among:
a phosphine of formula $PR^{16}R^{17}R^{18}$, wherein $R^{16}$-$R^{18}$ are independently selected among H, C1-C20 aliphatic group and C5-C20 aromatic groups;
and an optically active phosphine selected among (S)-neomenthyldiphenylphosphine and (R)-(+)-2-(diphenylphosphino)-2'-methoxy-1,1'-binaphthyl;
and at least one nitrogen-containing compound NN selected among

(Ia)

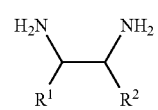

(Ib)

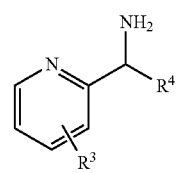

-continued

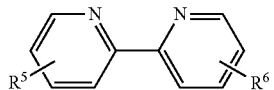
(Ic)

wherein
R¹-R⁶ are independently selected among H, C1-C20 aliphatic group and C5-C20 aromatic group, preferably R¹ and R² may be independently selected among H and a phenyl group and/or R³-R⁶ may be H.

According to a further embodiment, the present disclosure may refer to a process to obtain complexes of formula (VI) with the limitations described above.

Non limiting examples of preferred complexes of formula (VI) are:

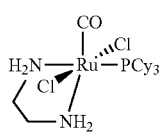
1

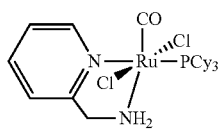
2

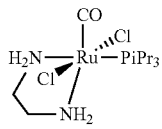
3

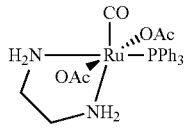
4

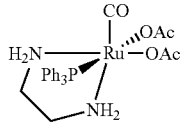
5

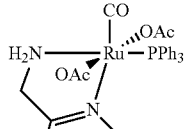
6

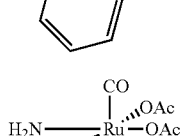
7

The synthesis of the monocarbonyl complexes 1-3 involves the use of t,t,t-RuCl₂(CO)(dmf)(PPh₃)₂ as starting product which can be prepared by reaction between the commercially available compound RuCl₂(PPh₃)₃ with CO in dimethylformamide (dmf). The complex 1 was obtained by reacting RuCl₂(CO)(dmf)(PPh₃)₂ with PCy₃ via the mixed phosphine intermediate RuCl₂(CO)(dmf)(PPh₃)(PCy₃) in CH₂Cl₂ and further addition of ethylenediamine, whereas reaction with 2-(aminomethyl)pyridine, in place of ethylenediamine, gave complex 2. Similarly, complex 3 was prepared using PiPr₃, in place of PCy₃, with ethylenediamine.

Similarly the complexes 4-7 of the invention were prepared from Ru(OAc)₂(CO)(PPh₃)₂ as starting product, which can be easily prepared on gram-scale by reaction between Ru(OAc)₂(PPh₃)₂ with CO in MeOH. The complexes 4 and 5 were obtained as a mixture by reacting Ru(OAc)₂(CO)(PPh₃)₂ with the ligand ethylenediamine in CH₂Cl₂, whereas reaction with 2-(aminomethyl)pyridine, in place of ethylenediamine, gave complexes 6 and 7 in a similar ratio of isomer (about 2/3, in favour of the cis-OAc isomers).

The activity in transfer hydrogenation of complex 2 is higher than that of complexes known in the art, such as RuCl₂(CO)(ampy)(PPh₃), reported by Cavarzan et al. (*Polyhedron* 2013, 62, 75), since the presence of the more basic phosphine allows the reduction at lower catalyst loading (S/C 5000 vs. 500).

According to an embodiment, the present disclosure may refer to a complex of formula (VII)

[MX(CO)(NN)(PP)]W (VII)

wherein M, X, W, (NN) and (PP) are as defined above and provided that when X is Cl or H, (NN) is not ethylenediamine or 2-(aminomethyl)pyridine and the diphosphine (PP) is not Ph₂P(CH₂CH₂CH₂)PPh₂.

According to a specific embodiment, the present disclosure may refer to complexes of formula (VII) wherein M, X, and (NN) are as defined above, provided that when X is Cl or H, the diphosphine (PP) may be selected among:
  ferrocene optionally substituted with C1-C20 aliphatic groups;
  an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane.

The present disclosure also refers to a process to obtain complexes of formula (VII) comprising reacting [MXY(CO)₂]n, MXY(CO)(PPh₃)₂ or MXY(CO)(PPh₃)₂(dmf), wherein M, X and Y are as defined above and (dmf) is dimethylformamide, with a diphosphine (PP) selected among:
  a diphosphine of formula P(R¹⁹)₂—Z—P(R²⁰)₂, wherein Z is a C2-C4 aliphatic group or ferrocene, optionally substituted with C1-C20 aliphatic groups, and wherein R¹⁹ and R²⁹ are independently selected among C1-C20 aliphatic groups and C5-C20 aromatic groups; and
  an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4- methoxyphenyl)phosphine]ferrocenyl}ethyldicyclohexyl phosphine and (2R,4R)-2,4-bis(diphenylphosphine)pentane;

and at least one nitrogen-containing compound NN selected among:

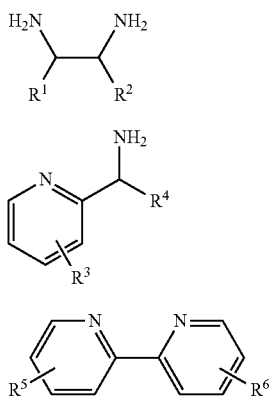

wherein
R$^1$-R$^6$ are independently selected among H, C1-C20 aliphatic group and C5-C20 aromatic group, preferably R$^1$ and R$^2$ may be independently selected among H and a phenyl group and/or R$^3$-R$^6$ may be H.

According to a preferred embodiment, the present disclosure may refer to a process to obtain a complex of formula (VII) wherein M is Ru and X=Y=Cl or acetate (OAc), by reacting [RuCl$_2$(CO)$_2$]$_n$ or RuCl$_2$(CO)(PPh$_3$)$_2$(dmf) or Ru(OAc)$_2$(CO)(PPh$_3$)$_2$ with a diphosphine (PP) selected among:

a diphosphine of formula P(R$^{19}$)$_2$—Z—P(R$^{20}$)$_2$, wherein Z is a C2-C4 aliphatic group or ferrocene, optionally substituted with C1-C20 aliphatic groups, wherein R$^{19}$ and R$^{29}$ are independently selected among C1-C20 aliphatic groups and C5-C20 aromatic groups; and an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane;

and at least one nitrogen-containing compound NN selected among:

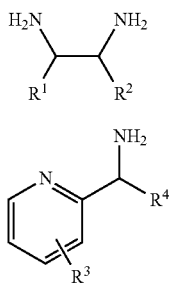

wherein
R$^1$-R$^6$ are independently selected among H, C1-C20 aliphatic group and C5-C20 aromatic group, preferably R$^1$ and R$^2$ may be independently selected among H and a phenyl group and/or R$^3$-R$^6$ may be H.

According to a further embodiment, the present disclosure may refer to a process to obtain complexes of formula (VII) with the limitations described above.

The synthetic route described above gives access to several diphosphine derivatives, including derivatives of achiral and chiral diphosphine ligands.

Non limiting examples of preferred complexes of formula (VII) are:

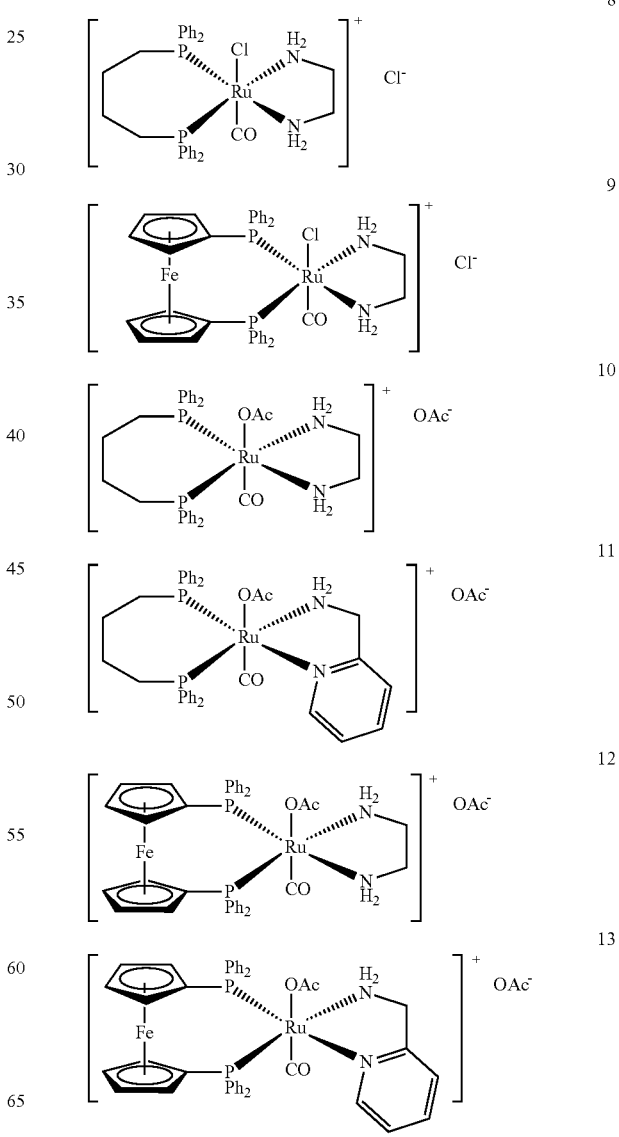

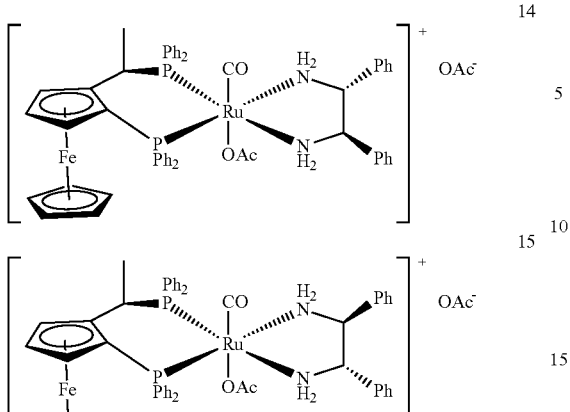

14

15

The cationic monocarbonyl derivatives 8 and 9 were obtained either from the polymer [RuCl$_2$(CO)$_2$]n, synthesized by reaction of RuCl$_3$·2.5H$_2$O with formic acid or from the complex RuCl$_2$(CO)(dmf)(PPh$_3$)$_2$. Reaction of [RuCl$_2$(CO)$_2$]n with 1,4-bis(diphenylphosphino) butane and ethylenediamine in 2-propanol led to 8, whereas using 1,1'-bis(diphenylphosphino) ferrocene, in place of 1,4-bis(diphenylphosphino) butane, gave 9. Reaction of RuCl$_2$(CO)(dmf)(PPh$_3$)$_2$ takes place in CH$_2$Cl$_2$ and affords the same products.

The cationic monocarbonyl derivatives 10-15 were obtained from the complex Ru(OAc)$_2$(CO)(PPh$_3$)$_2$ as starting product. The complex 10 was obtained by a one-pot reaction of Ru(OAc)$_2$(CO)(PPh$_3$)$_2$ with the ligands 1,4-bis(diphenylphosphino)butane and ethylenediamine in CH$_2$Cl$_2$. The complex 11 was obtained, in a similar manner, by using 2-(aminomethyl)pyridine in place of ethylenediamine. The complexes 12 and 13 were obtained using the ligand 1,1'-bis(diphenylphosphino)ferrocene in place of 1,4-bis(diphenylphosphino)butane and the ligands ethylenediamine and 2-(aminomethyl)pyridine, respectively.

Similarly the complexes 14 and 15 were obtained from the diphosphine (R)-1-[(Sp)-2-(diphenylphosphino)ferrocenylethyl]diphenylphosphine and the ligands (1R,2R)-1,2-diphenylethylenediamine and (1S,2S)-1,2-diphenylethylenediamine.

The ligands of the type HCNN (IIa-b) have the ability to act both as bidentate (IIa-b) or tridentate ligands of the type (IIc-d) when deprotonated.

According to an embodiment, in the case of bidentate ligand the coordination occurs through the nitrogen atom of the —NH$_2$ group and a second nitrogen atom of the heterocycle, in combination with a monophosphine to the metal. Thus, the present disclosure may refer to a complex of formula (VIII)

MXY(CO)(HCNN)(P) (VIII)

wherein M, X, Y, (HCNN) and (P) are as defined above.

Preferably, the monodentate phosphine (P) is a phosphine of formula PR$^{16}$R$^{17}$R$^{18}$, wherein R$^{16}$-R$^{18}$ are independently selected among H, C1-C20 aliphatic groups and C5-C20 aromatic groups.

The present disclosure also refers to a process to obtain complexes of formula (VIII) comprising reacting a compound of formula MXY(CO)(PPh$_3$)$_2$, or of formula MXY(CO)(PPh$_3$)$_2$(dmf), wherein M, X, Y are as defined above and (dmf) is dimethylformamide, with a nitrogen-containing compound HCNN selected among:

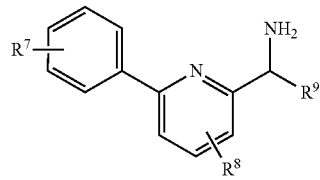

(IIa)

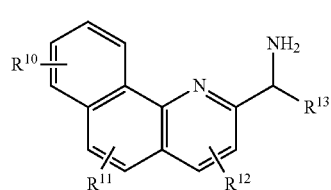

(IIb)

wherein

R$^7$-R$^{13}$ are independently selected among H, C1-C20 aliphatic groups, and C5-C20 aromatic groups, preferably R$^8$-R$^{13}$ may be H and/or R$^7$ may be 4-methyl, and optionally with a phosphine (P) selected among:

a phosphine of formula PR$^{16}$R$^{17}$R$^{18}$, wherein R$^{16}$-R$^{18}$ are independently selected among H, C1-C20 aliphatic groups and C5-C20 aromatic groups; and an optically active phosphine selected among (S)-neomenthyldiphenylphosphine and (R)-(+)-2-(diphenylphosphino)-2'-methoxy-1,1'-binaphthyl.

According to a preferred embodiment, the present disclosure may refer to a process to obtain a complex of formula (VIII) wherein M is Ru and X=Y=Cl or acetate (OAc) and P=PPh$_3$ by reacting RuCl$_2$(CO)(PPh$_3$)$_2$(dmf) or Ru(OAc)$_2$(CO)(PPh$_3$)$_2$ with a nitrogen-containing compound HCNN selected among:

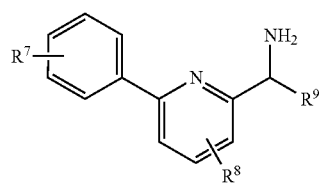

(IIa)

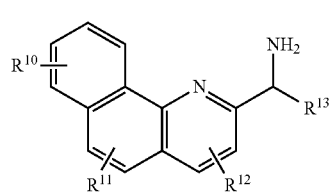

(IIb)

wherein

R$^7$-R$^{13}$ are independently selected among H, C1-C20 aliphatic group and C5-C20 aromatic group, preferably R$^8$-R$^{13}$ may be H and/or R$^7$ may be 4-methyl.

Examples of preferred complexes of formula (VIII) are:

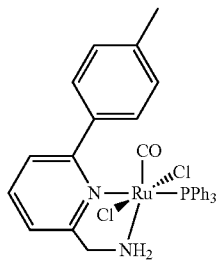
16

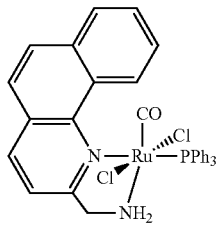
17

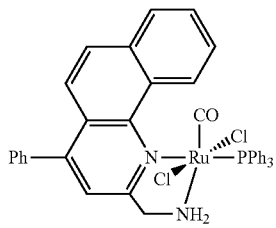
18

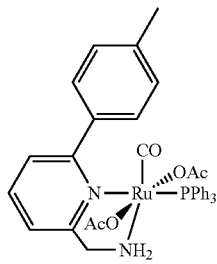
19

The monocarbonyl phosphine derivatives 16-18 were isolated from RuCl$_2$(CO)(PPh$_3$)$_2$(dmf) and 6-(4-methylphenyl)-2-(aminomethyl)pyridine, 2-(aminomethyl)benzo[h]quinoline and 4-phenyl-2-(aminomethyl) benzo[h]quinoline in CHCl$_3$.

The neutral acetate monocarbonyl triphenylphosphine derivative 19 was obtained by reacting Ru(OAc)$_2$(CO)(PPh$_3$)$_2$ and 6-(4-methylphenyl)-2-(aminomethyl)pyridine in toluene.

Known complexes such as RuCl$_2$(CO)(ampy)(PPh$_3$) (Cavarzan et al., *Polyhedron* 2013, 62, 75) shows remarkably lower activity and require a higher catalyst loading compared to compound 16 in transfer hydrogenation. The presence of the aromatic ring in the 6 position or the presence of a benzoquinoline ring leads to catalysts with a remarkably higher activity with respect to those containing the simple 2-(aminomethyl)pyridine ligand on account of the cyclometalation which occurs in the catalysis.

The HCNN ligands of the type (IIa), which contain a pyridine ring functionalized in the 6 position with an aromatic group, and those of the type (IIb), containing the benzo[h]quinoline system, have the ability to act as anionic tridentate ligands (IIc-d) through the nitrogen atom of the —NH$_2$ group, a second nitrogen atom of the heterocycle and a cyclometalated carbon atom with the metal. Thus, according to a further embodiment, the present disclosure may refer to complexes of formula (IX)

wherein M, X, (CNN) and (P) are as defined above.

The present disclosure also refers to a process to obtain complexes of formula (IX) by (i) reacting a compound of formula MXY(PPh$_3$)$_3$, wherein M, X and Y are as described above, with a nitrogen-containing ligand (CNN) of formula (IIc) or (IId)

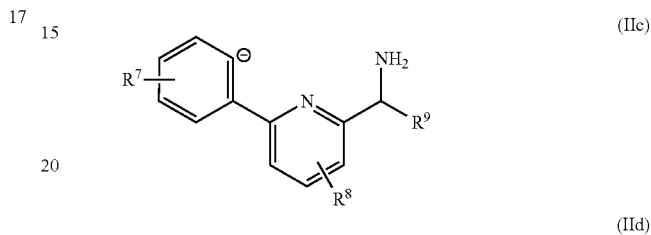

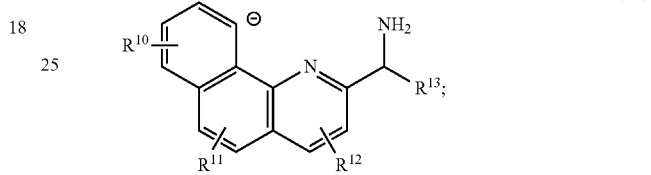

wherein

R$^7$-R$^{13}$ are independently selected among H, C1-C20 aliphatic group and C5-C20 aromatic group, preferably R$^8$-R$^{13}$ may be H and/or R$^7$ may be 4-methyl, and optionally a phosphine (P) selected among:

a phosphine of formula PR$^{16}$R$^{17}$R$^{18}$, wherein R$^{16}$-R$^{18}$ are independently selected among H, C1-C20 aliphatic groups and C5-C20 aromatic groups;

an optically active phosphine selected among (S)-neomenthyldiphenylphosphine and (R)-(+)-2-(diphenylphosphino)-2'-methoxy-1,1'-binaphthyl, thereby obtaining an intermediate derivative and (ii) reacting said derivative with CO.

According to a preferred embodiment, the present disclosure may refer to a process to obtain a complex of formula (IX) wherein M is Ru, X=Y=Cl and P=PPh$_3$ by reacting RuCl(CNN)(PPh$_3$)$_2$ with CO where CNN is a nitrogen-containing ligand CNN selected among

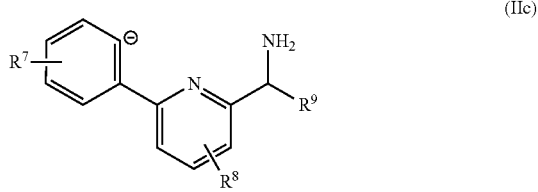

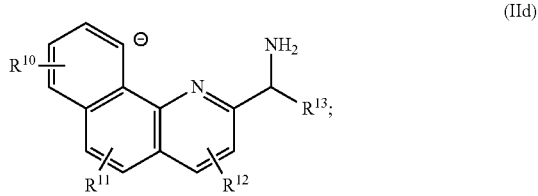

wherein

R⁷-R¹³ are independently selected among H, C1-C20 aliphatic group and C5-C20 aromatic group, preferably R⁸-R¹³ may be H and/or R⁷ may be 4-methyl.

RuCl(CNN)(PPh₃)₂ can be prepared according to processes known in the art, for example as described in WO2009/007443.

Non limiting examples of preferred complexes of formula (IX) are:

20

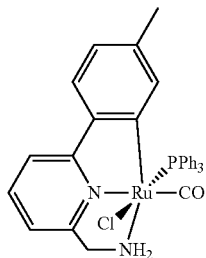

21

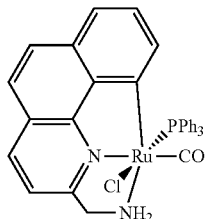

22

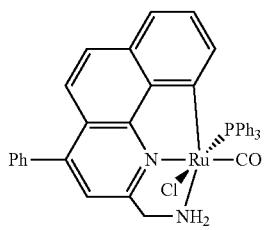

The monocarbonyl complexes 20-22 were obtained from the diphosphine pincer precursors RuCl(CNN)(PPh₃)₂ (CNN=amtp, ambq and ambq$^{Ph}$) by reaction with CO in CH₂Cl₂.

The anionic bidentate ligands of the type (IVb), obtained by deprotonation of an ortho-methyl group, have the ability through P and C atoms, in combination with a NN ligand, to coordinate ruthenium or osmium. Therefore, according to an embodiment, the present disclosure may refer to the complex of formula (X)

MX(CO)(NN)(CP)    (X)

wherein M, X, (NN) and (CP) are as defined above, with the proviso that when X is Cl, (NN) is not ethylenediamine or 2-(aminomethyl)pyridine and (CP) is not a compound of formula (IVb) in which R²¹=R²²=phenyl and R²³=methyl.

According to an embodiment, R²³ may be —CH₃ and/or R²¹-R²² may be C6-C20 cycloaliphatic group or C6-C20 aromatic group, more preferably R²³ may be —CH₃ and/or R²¹-R²² may be independently selected among phenyl and cyclohexyl group.

According to a further embodiment, the present disclosure may refer to a complex of formula (X) wherein M, X, (NN) and (CP) are as defined above, with the proviso that when X is Cl, R²¹ and R²² are not aromatic groups.

According to a further embodiment, the present disclosure may refer to a complex of formula (X) in which M, X, (NN) are as defined above, (CP) is a ligand of formula (IVb)

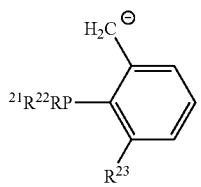

wherein

R²¹-R²³ are independently selected among H, C1-C20 aliphatic groups and C5-C20 aromatic groups, preferably R²³ may be —CH₃ and/or R²¹-R²² may be C6-C20 cycloaliphatic group or C6-C20 aromatic group, more preferably R²³ may be —CH₃ and/or R²¹-R²² may be independently selected among phenyl and cyclohexyl group;

with the proviso that when X is Cl, R²¹ and R²² are not aromatic groups.

The present disclosure refers also to a process to obtain complexes of formula (X) comprising:

(i) reacting MX₃.xH₂O with a HCP compound of formula (IVa)

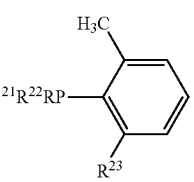

wherein

M and X are as defined above and R²¹-R²³ are independently selected among H, C1-C20 aliphatic groups and C5-C20 aromatic groups, thereby obtaining an intermediate complex of formula (XI), and (ii) reacting the complex of formula (XI) with a (NN) ligand of formula Ia to Ic:

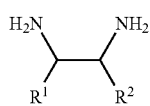

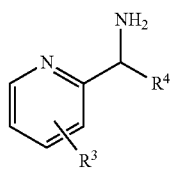

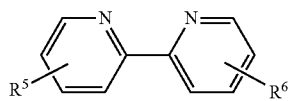

wherein

R¹-R⁶ are independently selected among H, C1-C20 aliphatic group and C5-C20 aromatic group, preferably R¹ and $R^2$ may be independently selected among H and a phenyl group and/or $R^3$-$R^6$ may be H.

According to a preferred embodiment, the present disclosure may refer to a process to obtain a complex of formula (X) wherein M is Ru and X is Cl, comprising:

(i) reacting $RuCl_3 \cdot xH_2O$ with a HCP compound of formula (IVa)

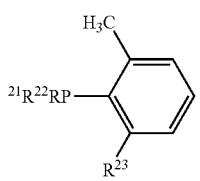
(IVa)

wherein $R^{21}$-$R^{23}$ are independently selected among H, C1-C20 aliphatic groups and C5-C20 aromatic groups, thereby obtaining an intermediate complex of formula (XI), and (ii) reacting the complex of formula (XI) with a (NN) ligand of formula (Ia-Ic):

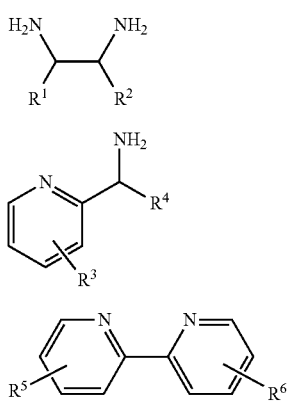

wherein $R^1$-$R^6$ are independently selected among H, C1-C20 aliphatic group and C5-C20 aromatic group, preferably $R^1$ and $R^2$ may be independently selected among H and a phenyl group and/or $R^3$-$R^6$ may be H.

According to a further embodiment, the present disclosure may refer to a process to obtain complexes of formula (X) with the limitations described above.

Non limiting examples of preferred complexes of formula (X) are:

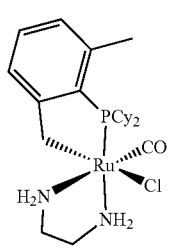
23

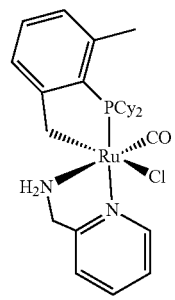
24

Complexes 23, 24 were synthesized from 25 by reaction with ethylenediamine or 2-(aminomethyl)pyridine, respectively, via displacement of the phosphine.

According to a further embodiment, the present disclosure may refer to a complex of formula (XI)

MX(CO)(CP)(HCP)     (XI)

wherein M, X, (CP) and (HCP) are as defined above and with the proviso that when X is Cl and $R^{23}$ is —$CH_3$, $R^{21}$ and $R^{22}$ are not phenyl groups. According to an embodiment, $R^{23}$ may be —$CH_3$ and/or $R^{21}$-$R^{22}$ may be C6-C20 cycloaliphatic group or C6-C20 aromatic group, preferably $R^{21}$-$R^{22}$ may be cyclohexyl groups.

According to a specific embodiment, the present disclosure may refer to complexes of formula (XI) wherein M, X, (CP) and (HCP) are as defined above, with the proviso that when X is Cl, $R^{21}$ and $R^{22}$ are not an aromatic groups.

The complex of formula (XI) is a pentacoordinate complex.

The present disclosure also refers to a process to obtain complexes of formula (XI) comprising reacting $MX_3 \cdot xH_2O$ with a HCP compound of formula (IVa)

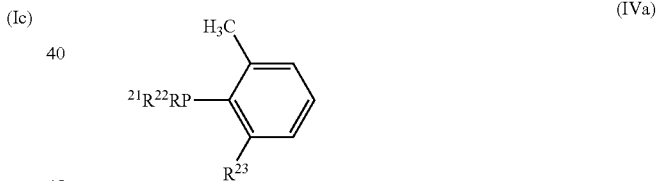
(IVa)

wherein

M and X are as defined above and $R^{21}$-$R^{23}$ are independently selected among H, C1-C20 aliphatic groups and C5-C20 aromatic groups, $R^{23}$ may be —$CH_3$ and/or $R^{21}$-$R^{22}$ may be C6-C20 cycloaliphatic group or C6-C20 aromatic group, preferably $R^{21}$-$R^{22}$ may be cyclohexyl groups.

According to a preferred embodiment, the present disclosure may refer to a process to obtain complexes of formula (XI) in which M is Ru and X is Cl by reacting $RuCl_3 \cdot xH_2O$ with a HCP compound of formula (IVa)

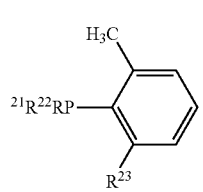
(IVa)

wherein
R²¹-R²³ are independently selected among H, C1-C20 aliphatic groups and C5-C20 aromatic groups, R²³ may be —CH₃ and/or R²¹-R²² may be C6-C20 cycloaliphatic group or C6-C20 aromatic group, preferably R²¹-R²² may be cyclohexyl groups.

According to an embodiment, the present disclosure may refer to a process to prepare complexes of formula (XI) with the limitations described above.

Non limiting examples of preferred complexes of formula (XI) is:

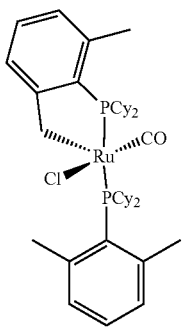

25

The complexes of formula (XI) may be synthesized using the anionic bidentate ligands of the type (IVb), obtained by deprotonation of an ortho-methyl group, which have the ability through P and C atoms, to coordinate ruthenium and osmium.

The cyclometallated monocarbonyl derivatives 25 was prepared by reaction of RuCl₃·xH₂O with (2,6-dimethylphenyl)dicyclohexylphosphine in ethanol and the presence of formaldehyde and triethylamine.

According to an embodiment, the present disclosure may refer to complexes of formula (XII)

MXY(CO)(PP)(P)                              (XII)

wherein M, X, Y, (PP) and (P) are as defined above. Preferably, (P) is triphenylphosphine.

The present disclosure also refers to a process to obtain the complexes of formula (XII) comprising reacting a compound of formula MXY(CO)(PPh₃)₂, or of formula MXY (CO)(PPh₃)₂(dmf), wherein M, X, Y are as defined above and (dmf) is dimethylformamide, with a phosphine (P) selected among:
  a phosphine of formula PR¹⁶R¹⁷R¹⁸, wherein R¹⁶-R¹⁸ are independently selected among H, C1-C20 aliphatic group and C5-C20 aromatic groups;
  an optically active phosphine selected among (S)-neomenthyldiphenylphosphine and (R)-(+)-2-(diphenylphosphino)-2'-methoxy-1,1'-binaphthyl;
  and a diphosphine (PP) selected among:
  a diphosphine of formula P(R¹⁹)₂—Z—P(R²⁰)₂, wherein Z is a C2-C4 aliphatic group or ferrocene optionally substituted with C1-C20 aliphatic groups, and wherein R¹⁹ and R²⁰ are independently selected among C1-C20 aliphatic groups and C5-C20 aromatic groups;
  an optically active diphosphine selected from the group consisting of (R)-(6,6'-dimethoxybiphenyl-2,2'-diyl)bis (diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane.

According to a preferred embodiment, the present disclosure refers to a process to obtain a complex of formula (XII) in which M is Ru and X is Cl or acetate group (OAc), by reacting RuCl₂(CO)(PPh₃)₂(dmf) or Ru(OAc)₂(CO)(PPh₃)₂ with a phosphine (P) selected among:
  a phosphine of formula PR¹⁶R¹⁷R¹⁸, wherein R¹⁶-R¹⁸ are independently selected among H, C1-C20 aliphatic group and C5-C20 aromatic groups;
  an optically active phosphine selected among (S)-neomenthyldiphenylphosphine and (R)-(+)-2-(diphenylphosphino)-2'-methoxy-1,1'-binaphthyl;
  and a diphosphine (PP) selected among:
  a diphosphine of formula P(R¹⁹)₂—Z—P(R²⁰)₂, wherein Z is a C2-C4 aliphatic group or ferrocene optionally substituted with C1-C20 aliphatic groups, and wherein R¹⁹ and R²⁰ are independently selected among C1-C20 aliphatic groups and C5-C20 aromatic groups;
  an optically active diphosphine selected from the group consisting of (R)-(6,6'-dimethoxybiphenyl-2,2'-diyl)bis (diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane.

Non limiting examples of preferred complexes of formula (XII) are:

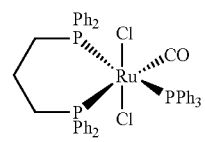

26

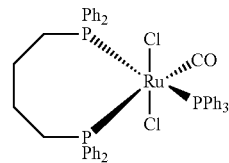

27

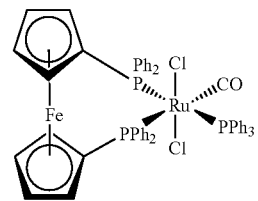

28

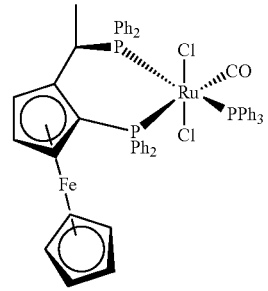

29

-continued

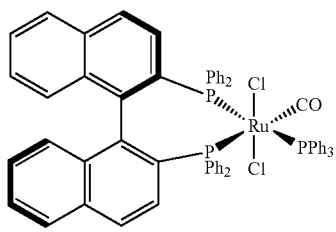

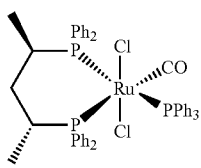

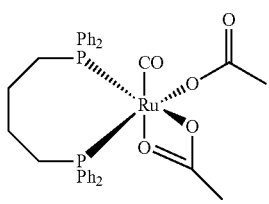

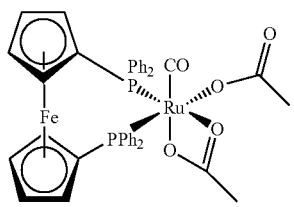

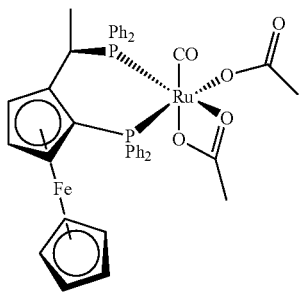

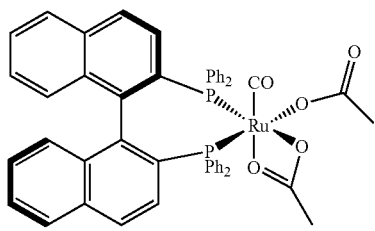

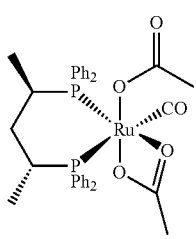

Complexes 26-36 have been synthesized by substitution of one or two triphenylphosphine from $RuCl_2(CO)(PPh_3)_2$ (dmf) or $Ru(OAc)_2(CO)(PPh_3)_2$.

In a further embodiment, the present disclosure may refer to a complex of formula (XIII)

$$MXY(CO)(HCN)(PP) \qquad (XIII)$$

wherein M, X, Y, (HCN) and (PP) are as defined above.

Preferably, the diphosphine (PP) is selected among a diphosphine of formula $P(R^{19})_2$—Z—$P(R^{20})_2$, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups.

The present disclosure also refers to a process to obtain a complex of formula (XIII) comprising reacting a compound of formula $MXY(CO)(PPh_3)_2$, or of formula $MXY(CO)(PPh_3)_2$(dmf), wherein M, X, Y are as defined above and (dmf) is dimethylformamide, with a diphosphine (PP) selected among:

a diphosphine of formula $P(R^{19})_2$—Z—$P(R^{20})_2$, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups;

an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane;

and a nitrogen-containing ligand (HCN) of formula IIIa

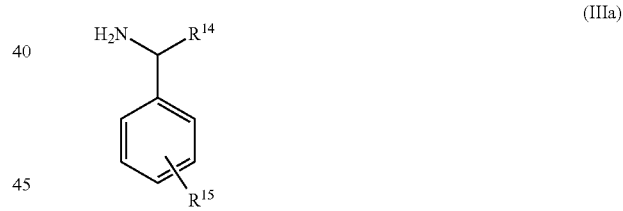

(IIIa)

wherein $R^{14}$ and $R^{15}$ are independently selected among H, C1-C20 aliphatic groups and C5-C20 aromatic groups, preferably $R^{14}$ and $R^{15}$ may be independently H.

According to a specific embodiment, the present disclosure refers to a process to obtain a complex of formula (XIII) in which M is Ru and X is Cl or acetate group, by reacting a compound of formula $RuCl_2(CO)(PPh_3)_2$(dmf) or $Ru(OAc)_2(CO)(PPh_3)_2$ with a phosphine (PP) selected among:

a diphosphine of formula $P(R^{19})_2$—Z—$P(R^{20})_2$, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups;

an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-

1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine) pentane;

and a nitrogen-containing ligand (HCN) of formula IIIa

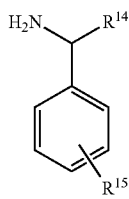

(IIIa)

wherein $R^1$-$R^{15}$ are independently selected among H, C1-C20 aliphatic groups and C5-C20 aromatic groups, preferably $R^{14}$ and $R^{15}$ may be independently H.

Non limiting examples of preferred complexes of formula (XIII) are:

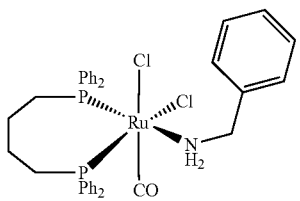

37

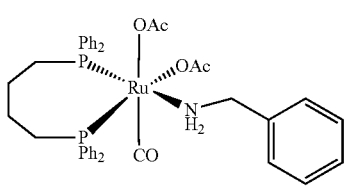

38

In a further embodiment, the present disclosure may refer to a complex of formula (XIV)

MXY(CO)(PNN)    (XIV)

wherein M, X, Y and (PNN) are as defined above.

According to a specific embodiment, the present disclosure may refer to complexes of formula (XIV) wherein M, X, Y and (PNN) are as defined above, provided that when X=Y, X and Y are not Cl.

The present disclosure also refers to a method to obtain the complexes of formula (XIV) comprising reacting a compound of formula MXY(CO)(PPh$_3$)$_2$, or of formula MXY(CO)(PPh$_3$)$_2$(dmf), wherein M, X, Y are as defined above and (dmf) is dimethylformamide with a tridentate (PNN) ligand of formula (V)

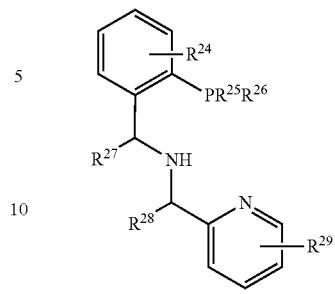

(V)

wherein $R^{24}$-$R^{29}$ are independently selected among H, C1-C20 alkyl group and C5-C20 aryl groups, preferably $R^{24}$ and $R^{27}$-$R^{29}$ may be H and/or $R^{25}$ and $R^{26}$ may be a C1-C20 aromatic group, more preferably a phenyl group.

According to a specific embodiment, the present disclosure may refer to a process to obtain a complex of formula (XIV) in which M is Ru and X is acetate group comprising reacting a compound of formula Ru(OAc)$_2$(CO)(PPh$_3$)$_2$ with a tridentate (PNN) ligand of formula (V)

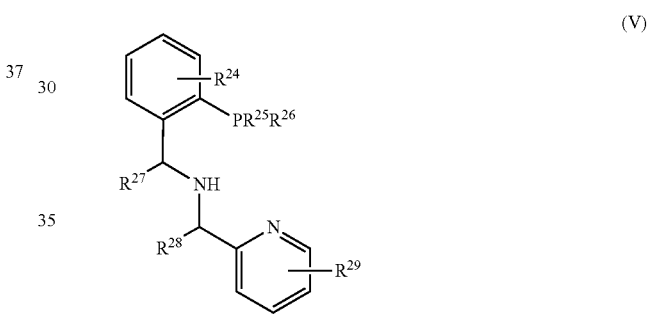

(V)

wherein $R^{24}$-$R^{29}$ are independently selected among H, C1-C20 alkyl groups and C5-C20 aryl groups, preferably $R^{24}$ and $R^{27}$-$R^{29}$ may be H and/or $R^{25}$ and $R^{26}$ may be a C1-C20 aromatic group, more preferably a phenyl group.

According to a further embodiment, the present disclosure may refer to a process to obtain a complex of formula (XIV) with the limitations described above.

A non-limiting example of complexes of formula (XIV) is:

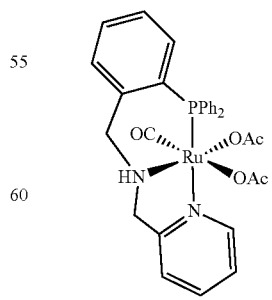

39

Complexes of formula (1) and sub-formulas (VI-XIV) have been found to be highly active in transfer hydrogenation of ketones and aldehydes and can be used in hydrogenation of the same compounds using molecular hydrogen.

A further aspect of the present disclosure is the use of the complex of formula (1) or of sub-formulas (VI-XIV) as catalysts or pre-catalyst for the reduction reaction of ketones or aldehydes to alcohols by transfer hydrogenation or hydrogenation with molecular hydrogen.

In another aspect, the present disclosure refers to a process for the reduction of ketones or aldehydes to the corresponding alcohols comprising the following steps:

(a) mixing a catalyst or pre-catalyst with a solution comprising at least one base and at least one substrate selected from the group consisting of C3-C42 ketones and C2-C41 aldehydes thereby obtaining a mixture; and (b) contacting said mixture with molecular $H_2$ or with at least one hydrogen-donor, preferably 2-propanol, sodium formate, ammonium formate, a mixture of formic acid and triethylamine, said process being characterized in that the catalyst or pre-catalyst is a pentacoordinate or a hexacoordinate complex of general formula (1):

wherein
M=Ru or Os;
a, b and d are independently 0 or 1;
cis 1 or 2;
X, Y are independently selected among halides, hydride, C1-C20 carboxylates and C1-C20 alkoxides;
W is selected among halides, C1-C20 carboxylates and C1-C20 alkoxides;
L is a nitrogen-containing ligand selected among:
(I) a NN compound of formula Ia to Ic:

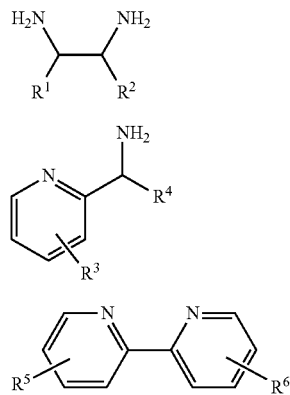

(II) a HCNN compound of formula IIa-IIb and a CNN ligand of formula IIc-IId:

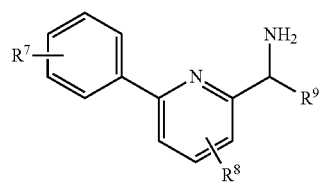

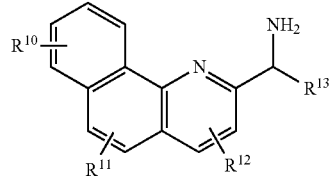

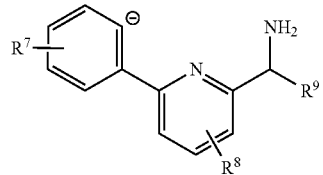

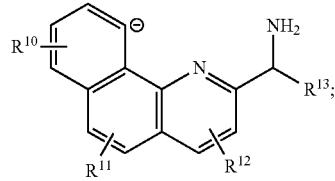

(III) a HCN compound of formula IIIa

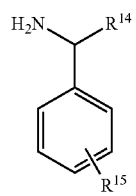

wherein
$R^1$-$R^{15}$ are independently selected among H, C1-C20 aliphatic groups and C5-C20 aromatic groups, preferably $R^1$ and $R^2$ may be independently selected among H and a phenyl group and/or $R^3$-$R^6$ and $R^8$-$R^{15}$ may be H and/or $R^7$ may be 4-methyl;
L' is at least one phosphorus-containing ligand selected among:
a phosphine (P) selected among: a phosphine of formula $PR^{16}R^{17}R^{18}$, wherein $R^{16}$-$R^{18}$ are independently selected among H, C1-C20 aliphatic groups and C5-C20 aromatic groups; an optically active phosphine selected among (S)-neomenthyldiphenylphosphine and (R)-(+)-2-(diphenylphosphino)-2'-methoxy-1,1'-binaphthyl,
a diphosphine (PP) selected among: a diphosphine of formula $P(R^{19})_2$—Z—$P(R^{20})_2$, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups; an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane, a HCP compound of formula (IVa) and a CP ligand of formula (IVb)

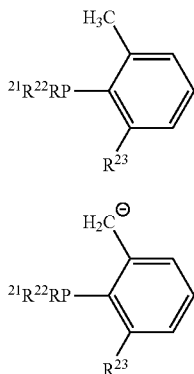

(IVa)

(IVb)

wherein
$R^{21}$-$R^{23}$ are independently selected among H, C1-C20 aliphatic groups and C5-C20 aromatic groups, $R^{23}$ may be —$CH_3$ and/or $R^{21}$-$R^{22}$ may be C6-C20 cycloaliphatic group or C6-C20 aromatic group, preferably $R^{21}$-$R^{22}$ may be cyclohexyl groups;
a PNN compound of formula (V)

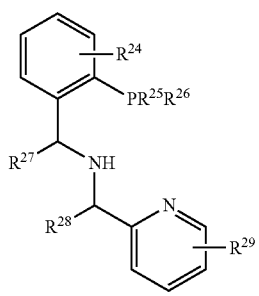

(V)

wherein
$R^{24}$-$R^{29}$ are independently selected among H, C1-C20 aliphatic groups and C5-C20 aromatic groups, preferably $R^{24}$ and $R^{27}$-$R^{29}$ may be H and/or $R^{25}$ and $R^{26}$ may be a C1-C20 aromatic group, more preferably a phenyl group.

According to a further embodiment, the present disclosure may refer to a process for the reduction of ketones or aldehydes to the corresponding alcohols, wherein the catalyst or pre-catalyst is a pentacoordinate or a hexacoordinate complex of general formula (1) with at least one of the limitations described above.

The complex of formula (1) containing only phosphorus-containing ligands L' is conveniently used as pre-catalyst in transfer hydrogenation or hydrogenation with molecular hydrogen, wherein the (transfer)hydrogenation is carried out in the presence of a nitrogen-containing ligand L.

Therefore, according to an embodiment, the present disclosure refers to a process for the reduction of ketones or aldehydes to the corresponding alcohols, comprising the following steps:
(a) mixing a pre-catalyst with a solution comprising at least one base and at least one substrate selected from the group consisting of C3-C42 ketones and C2-C41 aldehydes thereby obtaining a mixture; and (b) contacting said mixture with molecular $H_2$ or with at least one hydrogen-donor, preferably 2-propanol, sodium formate, ammonium formate, a mixture of formic acid and triethylamine,
wherein said pre-catalyst has general formula (2):

$$[MXY_a(CO)L'_c]W_d \qquad (2)$$

wherein
M=Ru or Os;
a, b and d are independently 0 or 1;
c is 1 or 2;
X, Y are independently selected among halides, hydride, C1-C20 carboxylates and C1-C20 alkoxides;
W is selected among halides, C1-C20 carboxylates and C1-C20 alkoxides;
L' is at least one phosphorus-containing ligand selected among:
a phosphine (P) selected among: a phosphine of formula $PR^{16}R^{17}R^{18}$, wherein $R^{16}$-$R^{18}$ are independently selected among H, C1-C20 aliphatic groups and C5-C20 aromatic groups; an optically active phosphine selected among (S)-neomenthyldiphenylphosphine and (R)-(+)-2-(diphenylphosphino)-2'-methoxy-1,1'-binaphthyl,
a diphosphine (PP) selected among: a diphosphine of formula $P(R^{19})_2$—Z—$P(R^{20}$ 2, wherein Z is a C2-C4 aliphatic group or ferrocene optionally substituted with C1-C20 aliphatic groups, and wherein $R^{19}$ and $R^{20}$ are independently selected among C1-C20 aliphatic groups and C5-C20 aromatic groups; an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane,
a HCP compound of formula (IVa) and a CP ligand of formula (IVb)

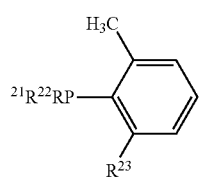

(IVa)

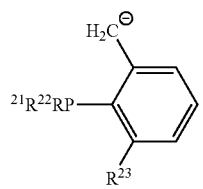

(IVb)

wherein
$R^{21}$-$R^{23}$ are independently selected among H, C1-C20 aliphatic groups and C5-C20 aromatic groups $R^{23}$ may be —$CH_3$ and/or $R^{21}$-$R^{22}$ may be C6-C20 cycloaliphatic group or C6-C20 aromatic group, preferably $R^{21}$-$R^{22}$ may be cyclohexyl groups
and wherein step (a) is carried out by mixing said pre-catalyst with a solution further comprising at least one nitrogen-containing compound L selected among:

(i) a NN compound of formula Ia to Ic:

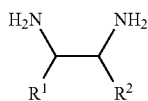
(Ia)

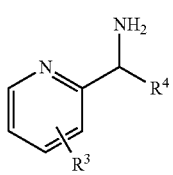
(Ib)

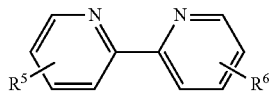
(Ic)

(ii) a HCNN compound of formula IIa-IIb and a CNN ligand of formula IIc-IId:

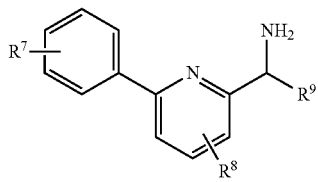
(IIa)

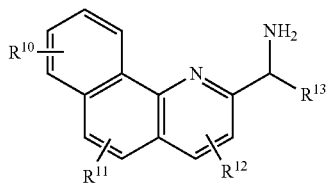
(IIb)

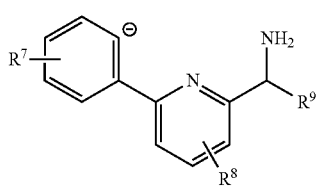
(IIc)

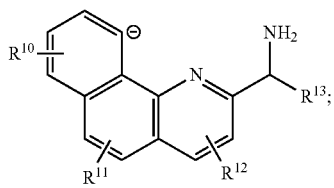
(IId);

(iii) a HCN compound of formula IIIa

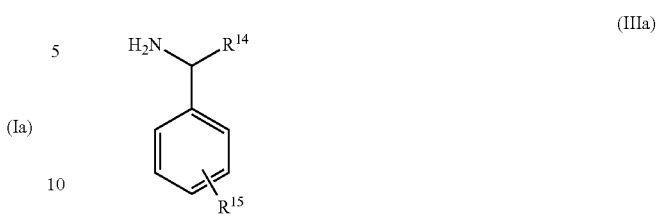
(IIIa)

(iv) a PNN compound of formula (V)

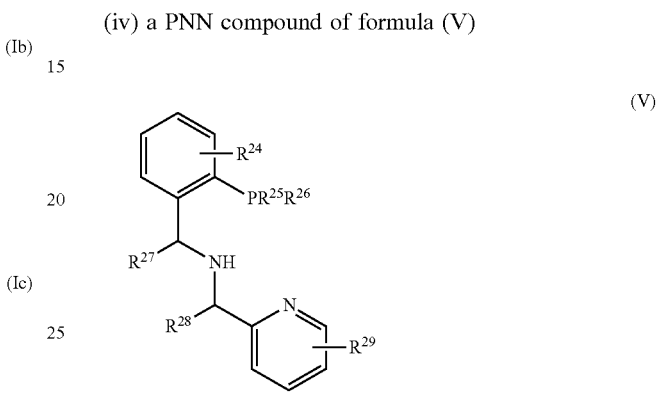
(V)

wherein
$R^1$-$R^{15}$ and $R^{24}$-$R^{29}$ are independently selected among H, C1-C20 aliphatic groups and C5-C20 aromatic groups, preferably $R^1$ and $R^2$ and $R^{24}$-$R^{29}$ may be independently selected among H and a phenyl group and/or $R^3$-$R^6$ and $R^8$-$R^{15}$ may be H and/or $R^7$ may be 4-methyl.

Preferably, the nitrogen-containing compound is selected among NN compounds of formula (Ia) to (Ic)

(Ia)

(Ib)

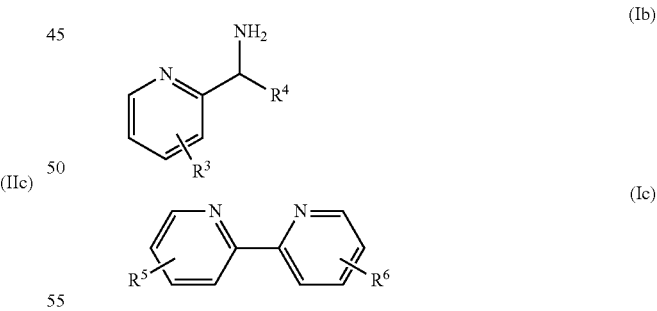
(Ic)

wherein $R^1$-$R^6$ are independently selected among H, C1-C20 aliphatic groups and C5-C20 aromatic groups. More preferably, the nitrogen-containing compound is selected among ethylenediamine and 2-(aminomethyl)pyridine.

According to an embodiment, the step (a) of the processes described above may be conducted in the presence of a base, wherein said base may be potassium hydroxide, potassium carbonate or an alkali metal alkoxide preferably selected among sodium iso-propoxide, potassium tert-butoxide, more preferably is potassium tert-butoxide, and in step (b) the mixture is contacted with molecular hydrogen.

According to a further embodiment, in the process of the disclosure in step (a) the base is sodium iso-propoxide and in step (b) the mixture is contacted with at least one hydrogen donor.

The transfer hydrogenation reduction process of the present disclosure may be carried out at a temperature of 30-82° C.

In one embodiment, the reduction reactions by hydrogenation may be carried out at 40-70° C. under hydrogen atmosphere (5-30 atm) in presence of methanol or ethanol as solvent. Under these reaction conditions the conversion of the ketone or aldehyde to alcohol is good to complete.

The complex of the present disclosure can be used for the preparation of alcohols, also chiral, by the reduction of C3-C41 ketones and of C2-C41 aldehydes.

In the process of the disclosure, the substrate may be:
at least one C3-C41 ketone selected among compounds of formula $R^{30}C(=O)R^{31}$ wherein $R^{30}$ and $R^{31}$ are independently selected among C1-C20 aliphatic, substituted aliphatic, aromatic, substituted aromatic and heteroaromatic groups wherein optionally $R^{30}$ and $R^{31}$ are linked to form a cycle;
at least one C2-C41 aldehyde is selected among compounds of formula $R^{32}C(=O)H$, wherein $R^{32}$ is selected among C1-C40 aliphatic, substituted aliphatic, aromatic, substituted aromatic and heteroaromatic groups; and
mixtures thereof.

According to an embodiment, in the process of the present disclosure the molar ratio substrate/catalyst or pre-catalyst may range from 1000/1 to 100000/1, preferably from 1000/1 to 50000/1.

According to a further embodiment, in the process of the present disclosure the molar ratio substrate/base may range from 10/1 to 100/1.

In a further embodiment, the present disclosure may refer to complexes of formula (1) and (2) and of sub-formulas (VI)-(XIV) as described above in which M is Ru.

In a further embodiment, the present disclosure may refer to complexes of formula (1) and (2) and of sub-formulas (VI-XIV) as described above, wherein X and Y are equal. More preferably, the present disclosure may refer to complexes of formula (1) and (2) and of sub-formulas (VI-XIV) as described above, wherein X and Y are equal and are selected among Cl and acetate group.

In a further embodiment, the present disclosure may refer to a complex of formula (1) and (2) and of sub-formula (VII) as described above, wherein W is chlorine.

These and other objects as well as features and advantages of the present invention will be better understood from the following detailed description and from the preferred embodiments which are given for illustrative purposes and not limitative of the invention itself.

Example 1: Synthesis of the Complex $RuCl_2(CO)(En)(PCy_3)$ (1)

The complex $RuCl_2(CO)(dmf)(PPh_3)_2$ (250 mg, 0.31 mmol, 1 equiv), suspended in 5 mL of dichloromethane, was reacted with $PCy_3$ (176 mg, 0.63 mmol, 2 equiv). After stirring the mixture for 3 hours at room temperature, the ligand en (25 μL, 0.37 mmol, 1.2 equiv) was added and the solution was stirred for 3 hours at room temperature. The volume was reduced to about half and the complex was precipitated by adding 5 mL of pentane. The obtained solid was filtered, washed 2 times with 10 mL of ethyl ether and dried under reduced pressure. Yield: 149 mg (89%). Anal. Calcd (%) for $C_{21}H_{41}Cl_2N_2OPRu$:C, 46.66; H, 7.65; N, 5.18, Found: C, 46.39; H, 7.49; N, 5.36. $^1H$ NMR (200 MHz, $CD_2Cl_2$) δ 3.77-3.62 (m, 2H), 3.35-3.20 (m, 2H), 3.09 (dd, J=10.9, 5.5 Hz, 2H), 2.92 (dd, J=9.7, 6.0 Hz, 2H), 2.32-1.08 (m, 33H). $^{13}C$ NMR (50 MHz, $CD_2Cl_2$) δ 206.0 (d, J=16.8 Hz), 43.5 (d, J=2.8 Hz), 42.3 (d, J=1.5 Hz), 35.3 (d, J=21.0 Hz), 29.7, 28.2 (d, J=10.0 Hz), 27.0. $^{31}P$ NMR (81.0 MHz, $CD_2Cl_2$) δ 45.5. IR (cm$^{-1}$): 1936.

Example 2: Synthesis of the Complex $RuCl_2(CO)(ampy)(PCy_3)$ (2)

The complex $RuCl_2(CO)(dmf)(PPh_3)_2$ (300 mg, 0.38 mmol, 1 equiv), suspended in 5 mL of dichloromethane, was reacted with the ligand $PCy_3$ (210 mg, 0.75 mmol, 2 equiv). After stirring the mixture for 3 hours at room temperature, the ligand ampy (47 μL, 0.45 mmol, 1.2 equiv) was added. The solution was stirred for 3 hours at room temperature, the volume was reduced to about half and the complex was precipitated by adding 5 mL of pentane. The obtained solid was filtered, washed 2 times with 10 mL of ethyl ether and dried under reduced pressure. Yield: 187 mg (84%). Anal. Calcd (%) for $C_{25}H_{41}Cl_2OPRu$:C, 51.02; H, 7.02; N, 4.76, Found: C, 51.26; H, 7.22; N, 4.57. $^1H$ NMR (200 MHz, $CD_2Cl_2$) δ 9.11 (d, J=5.5 Hz, 1H), 7.88-7.62 (m, 1H), 7.55-7.28 (m, 1H), 7.28-7.10 (m, 1H), 4.70 (t, J=5.9 Hz, 2H), 4.20 (t, J=5.6 Hz, 2H), 2.33 (ddt, J=23.4, 12.1, 2.8 Hz, 3H), 2.18-1.06 (m, 30H). $^{13}C$ NMR (50 MHz, $CD_2Cl_2$) 207.5 (d, J=17.8 Hz), 160.1, 152.55, 137.6, 124.4 (d, J=2.2 Hz), 121.7 (d, J=2.0 Hz), 50.6 (d, J=2.3 Hz), 34.5 (d, J=21.1 Hz), 29.5, 28.1 (d, J=10.1 Hz), 27.0. $^{31}P$ NMR (81.0 MHz, $CD_2Cl_2$) δ 45.9. IR (cm$^{-1}$): 1941.

Example 3: Synthesis of the Complex $RuCl_2(CO)(en)(PiPr_3)$ (3)

The complex $RuCl_2(CO)(dmf)(PPh_3)_2$ (81.7 mg, 0.10 mmol, 1 equiv), suspended in 5 mL of distilled dichloromethane, was reacted with the ligand $PiPr_3$ (25 μL, 0.13 mmol, 1.3 equiv). After stirring the mixture for 3 hours at room temperature, the ligand en (11 μL, 0.16 mmol, 1.6 equiv) was added. The solution was stirred for 3 hours at room temperature. The volume was reduced to about half and the complex was precipitated by adding 5 mL of pentane. The obtained solid was filtered, washed 2 times with 10 mL of ethyl ether and dried at reduced pressure. Yield: 28 mg (66%). Anal. Calcd (%) for $Cl_2H_{29}Cl_2N_2OPRu$:C, 34.29; H, 6.95; N, 6.66, Found: C, 34.00; H, 7.20; N, 6.60. $^1H$ NMR (200 MHz, $CD_2Cl_2$) δ 3.70-3.51 (m, 2H), 3.39-3.23 (m, 2H), 3.09 (dd, J=11.2, 5.7 Hz, 2H), 3.01-2.85 (m, 2H), 2.63-2.39 (m, 3H), 1.33 (dd, J=13.1, 7.3 Hz, 18H). $^{13}C$ NMR (50 MHz, $CD_2Cl_2$) δ 205.8 (d, J=17.0 Hz), 43.5 (d, J=2.9 Hz), 42.2 (d, J=1.7 Hz), 25.1 (d, J=22.4 Hz), 19.6 (d, J=0.7 Hz). $^{31}P$ NMR (81.0 MHz, $CD_2Cl_2$) δ 55.8. IR (cm$^{-1}$): 1921.

Example 4: Synthesis of the Complex $Ru(OAc)_2(CO)(en)(PPh_3)$ (4 and 5)

The complex $Ru(OAc)_2(CO)(PPh_3)_2$ (150 mg, 0.19 mmol, 1 equiv) suspended in $CH_2Cl_2$ (2 mL) was reacted with the ligand en (16 μL, 0.24 mmol, 1.2 equiv). After stirring the mixture for 2 h at room temperature, the volume was reduced to about half and the complex was precipitated by adding 10 mL of n-heptane. The obtained solid was filtered, washed 3 times with ethyl ether (3 mL), once with n-pentane (3 mL) and dried under reduced pressure. Yield:

64 mg (58%) as a mixture of cis and trans complexes 4 and 5, in 2/3 ratio respectively. Anal. Calcd (%) for $C_{25}H_{29}N_2O_5PRu$: C, 52.72; H, 5.13; N, 4.92, Found: C, 52.90; H, 5.02; N, 5.14. $^1H$ NMR (200 MHz, $CD_2Cl_2$) δ 7.92-7.20 (m, 21H), 7.06-6.84 (m, 0.4H), 5.28-5.13 (m, 0.4H), 5.04-4.85 (m, 2H), 4.01-3.78 (m, 2H), 3.23-3.04 (m, 0.4H), 2.88-2.75 (m, 0.4H), 2.75-2.57 (m, 2.8H), 2.54-2.37 (m, 2.8H), 1.98 (s, 1.2H), 1.62 (s, 6H), 1.58 (s, 1.2H). $^{13}C$ NMR (50 MHz, $CD_2Cl_2$) δ 205.1 (d, J=17.9 Hz), 204.7 (d, J=17.9 Hz), 181.6, 180.4, 179.4, 134.4 (d, J=1.3 Hz), 134.0 (d, J=10.4 Hz), 133.8 (d, J=10.5 Hz), 133.5 (d, J=1.3 Hz), 133.2 (d, J=1.0 Hz), 130.3, 130.3, 128.8 (d, J=3.8 Hz), 128.6 (d, J=3.7 Hz), 46.8 (d, J=3.1 Hz), 44.5 (d, J=2.4 Hz), 44.0 (d, J=1.9 Hz), 43.4 (d, J=4.1 Hz), 25.3, 24.4, 24.3. $^{31}P$ NMR (81.0 MHz, $CD_2Cl_2$) δ 51.6, 47.3. IR ($cm^{-1}$): 1934, 1924.

Example 5: Synthesis of the Complex $Ru(OAc)_2(CO)(ampy)(PPh_3)$ (6 and 7)

The complex $Ru(OAc)_2(CO)(PPh_3)_2$ (150 mg, 0.19 mmol, 1 equiv) suspended in $CH_2Cl_2$ (2 mL) was reacted with the ligand Ampy (25 μL, 0.24 mmol, 1.2 equiv). After stirring the mixture for 2 h at room temperature, the volume was reduced to about half and the complex was precipitated by adding 10 mL of n-heptane. The obtained solid was filtered, washed 3 times with ethyl ether (3 mL), once with n-pentane (3 mL) and dried under reduced pressure. Yield: 77 mg (64%) as a mixture of 6 and 7 in a 2/3 ratio respectively. Anal. Calcd (%) for $C_{29}H_{29}N_2O_5PRu$: C, 56.40; H, 4.73; N, 4.54, Found: C, 56.75; H, 4.59; N, 4.23. $^1H$ NMR (200 MHz, $CD_2Cl_2$) δ 9.49-9.42 (m, 0.7H), 9.10-8.66 (m, 0.7H), 8.59-8.48 (m, 1H), 7.83-7.22 (m, 25H), 5.40 (t, J=5.7 Hz, 1.4H), 4.21 (t, J=6.2 Hz, 1.4), 4.08 (dd, J=16.2, 5.0 Hz, 1H), 3.87 (ddd, J=15.7, 9.8, 5.8 Hz, 1H), 2.08 (s, 2.1H), 2.01 (s, 2.1H), 1.43 (s, 3H), 1.33 (s, 3H). $^{13}C$ NMR (50 MHz, $CD_2Cl_2$) δ 205.8 (d, J=17.7 Hz), 205.5 (d, J=18.9 Hz), 182.1, 179.8, 177.8, 163.4, 161.3 (d, J=1.8 Hz), 154.7, 150.3, 138.5, 138.0, 134.2 (d, J=10.5 Hz), 134.1 (d, J=10.5 Hz), 133.4, 133.0, 132.5, 130.5 (d, J=2.3 Hz), 130.4 (d, J=2.5 Hz), 128.8 (d, J=9.8 Hz), 128.6 (d, J=9.8 Hz), 124.2 (d, J=2.8 Hz), 123.6 (d, J=2.4 Hz), 121.2 (d, J=1.8 Hz), 121.0 (d, J=1.4 Hz), 52.9 (d, J=2.3 Hz), 49.5 (d, J=3.5 Hz), 25.0, 24.3, 24.1. $^{31}P$ NMR (81.0 MHz, $CD_2Cl_2$) δ 53.8, 49.8. IR ($cm^{-1}$): 1945, 1923.

Example 6: Synthesis of the Complex [RuCl(CO)(en)(dppb)]Cl (8)

The complex $[RuCl_2(CO)_2]_n$ (50 mg, 0.22 mmol, 1 equiv) suspended in 5 mL of distilled isopropanol, was reacted with the ligand dppb (94 mg, 0.22 mmol, 1 equiv). After stirring the mixture for 2 hours at 90° C., the ligand en (15 μL, 0.22 mmol, 1 equiv) was added and stirred for further 2 hours at 90° C. The solution was evaporated in vacuum, and the solid was dissolved in $CHCl_3$ (3 mL) and stirred for 3 hours at room temperature. The volume was reduced by half, the complex was precipitated by adding 5 mL of pentane. The obtained solid was filtered, washed 2 times with 10 mL of ethyl ether and dried at reduced pressure. Yield: 151 mg (98%). Anal. Calcd (%) for $C_{32}H_{36}ClN_2O_2P_2Ru$: C, 56.60; H, 5.34; N, 4.13, Found: C, 56.59; H, 5.39; N, 4.20. $^1H$ NMR (200 MHz, $CDCl_3$) δ 7.84-7.65 (m, 4H), 7.56-7.29 (m, 16H), 3.68-3.37 (m, 2H), 3.05-2.74 (m, 4H), 2.65-2.35 (m, 4H), 2.18-1.87 (m, 2H), 1.76-1.52 (m, 4H). $^{13}C$ NMR (50 MHz, $CD_2Cl_2$) δ 199.5 (t, J=13.6 Hz), 137.1 (t, J=13.8 Hz), 135.9 (t, J=13.9 Hz), 134.6 (t, J=5.1 Hz), 131.6 (d, J=3.6 Hz), 130.4, 129.3 (t, J=4.6 Hz), 129.0 (t, J=5.0 Hz), 45.9, 25.5 (t, J=13.8 Hz), 24.9 (t, J=16.2 Hz), 22.1. $^{31}P$ NMR (81.0 MHz, $CD_2Cl_2$) δ 37.4. IR ($cm^{-1}$): 1969.

Example 7: Synthesis of the Complex [RuCl(CO)(en)(dppf)]Cl (9)

The complex $RuCl_2(CO)(dmf)(PPh_3)_2$ (200 mg, 0.25 mmol, 1 equiv) dissolved in $CH_2Cl_2$ (2 mL) was reacted with the ligand dppf (160 mg, 0.29 mmol, 1.2 equiv) at room temperature for 2 h. The ligand en (15 μL, 0.37 mmol, 1.5 equiv) was then added and the mixture was stirred at room temperature for 2 h. The solution was concentrated to about 0.5 mL and the complex was precipitated by addition of n-heptane (10 mL). The obtained solid was filtered and thoroughly washed 4 times with ethyl ether (3 mL) and dried under reduced pressure. Yield: 180 mg (88%). Anal. Calcd (%) for $C_{37}H_{36}Cl_2FeN_2OP_2Ru$: C, 54.56; H, 4.46; N, 3.44, Found: C, 54.50; H, 4.51; N, 3.47. $^1H$ NMR (200 MHz, $CD_2Cl_2$) δ 7.97-7.24 (m, 20H), 5.59 (s, 2H), 5.15-4.91 (m, 2H), 4.53 (s, 2H), 4.20 (s, 2H), 3.97 (s, 2H), 3.68-3.42 (m, 2H), 2.58-2.41 (m, 2H), 2.14-1.85 (m, 2H). $^{13}C$ NMR (50 MHz, $CD_2Cl_2$) δ 204.0 (t, J=14.8 Hz), 135.9 (t, J=5.7 Hz), 134.2, 134.1 (d, J=10.1 Hz), 133.4, 132.9 (t, J=4.7 Hz), 132.0, 130.7, 130.4 (d, J=2.4 Hz), 129.2-128.3 (m), 77.8 (t, J=4.9 Hz), 75.7 (t, J=3.2 Hz), 73.5 (t, J=3.3 Hz), 71.3 (t, J=3.0 Hz), 45.7. $^{31}P$ NMR (81.0 MHz, $CD_2Cl_2$) δ 39.8. IR ($cm^{-1}$): 1960.

Example 8: Synthesis of the Complex [Ru(OAc)(CO)(en)(dppb)]OAc (10)

The complex $Ru(OAc)_2(CO)(PPh_3)_2$ (200 mg, 0.26 mmol, 1 equiv) suspended in $CH_2Cl_2$ (2 mL) was reacted with the ligand dppb (120 mg, 0.29 mmol, 1.1 equiv) at room temperature for 6 h. The ligand en (25 μL, 0.37 mmol, 1.4 equiv) was added and the solution was stirred at room temperature for further 2 h. The solution was concentrated to about 0.5 mL and the complex was precipitated by addition of n-heptane (10 mL). The obtained solid was filtered and washed 4 times with ethyl ether (3 mL) and dried under reduced pressure. Yield: 182 mg (97%). Anal. Calcd (%) for $C_{35}H_{42}N_2O_5P_2Ru$: C, 57.29; H, 5.77; N, 3.82 Found: C, 57.70; H, 5.90; N, 3.50. $^1H$ NMR (200 MHz, $CD_3OD$) δ 7.64-7.30 (m, 21H), 4.76-4.62 (m, 1H), 4.30-4.14 (m, 1H), 4.10-3.92 (m, 1H), 2.92-2.47 (m, 6H), 1.86 (s, 3H), 1.58 (s, 3H), 1.31-1.18 (m, 2H). $^{13}C$ NMR (50 MHz, $CD_3OD$) δ 203.8 (t, J=17.7 Hz), 182.7, 182.5, 134.8 (d, J=10.5 Hz), 134.4-134.1 (m), 133.8-133.6 (m), 132.3, 131.7, 131.2 (d, J=2.3 Hz), 130.1 (t, J=4.8 Hz), 129.8 (t, J=4.8 Hz), 129.4 (d, J=9.7 Hz), 46.6 (d, J=10.6 Hz), 44.7 (d, J=11.0 Hz), 30.1 (d, J=6.7 Hz), 29.6 (d, J=14.2 Hz), 25.5, 24.0, 23.5. $^{31}P$ NMR (81.0 MHz, $CD_3OD$) δ 37.1. IR ($cm^{-1}$): 1939.

Example 9: Synthesis of the Complex [Ru(OAc)(CO)(ampy)(dppb)]OAc (11)

In an NMR tube the complex $Ru(OAc)_2(CO)(dppb)$ (32) (31 mg, 0.05 mmol, 1 equiv) suspended in 0.6 mL of toluene-$d_8$, was reacted with the ligand ampy (5 μL, 0.05 mmol, 1 equiv). After stirring the mixture at room temperature for 30 min, the sample was characterized by NMR. The sample was then dried under low pressure. Yield: 31.3 mg (87%). Anal. Calcd (%) for $C_{39}H_{42}N_2O_5P_2Ru$: C, 59.92; H, 5.42; N, 3.58 Found: C, 60.30; H, 5.60; N, 3.20. $^1H$ NMR (200 MHz, toluene-$d_8$) δ 8.19-7.94 (m, 4H), 7.61-6.80 (m, 17H), 6.68-6.55 (m, 1H), 6.47 (dd, J=7.0, 5.1 Hz, 1H), 6.33-6.06 (m, 1H), 4.20 (t, J=17.4 Hz, 1H), 3.20 (t, J=12.0

Hz, 1H), 3.07-2.86 (m, 1H), 2.66-2.42 (m, 1H), 2.03 (s, 3H), 1.93 (s, 3H), 1.84-1.56 (m, 3H), 1.48-1.12 (m, 5H). $^{13}$C NMR (50 MHz, toluene-d$_8$) δ 203.3, 187.6, 177.0, 163.2, 159.8, 149.1 (d, J=22.9 Hz), 135.6, 134.9-132.0 (m), 130.5-129.4 (m), 121.3 (d, J=13.4 Hz), 121.3, 120.8, 50.4, 30.7, 30.1, 29.9, 29.4, 25.8, 24.6 (d, J=4.2 Hz). $^{31}$P NMR (81.0 MHz, toluene-d$_8$) 46.4 (d, J=28.8 Hz), 34.0 (d, J=29.0 Hz). IR (cm$^{-1}$): 1944, 1608, 1586.

Example 10: Synthesis of the Complex [Ru(OAc)(CO)(en)(dppf)]OAc (12)

In an NMR tube the complex Ru(OAc)$_2$(CO)(dppf) (33) (31.9 mg, 0.04 mmol, 1 equiv) suspended in 0.6 mL of toluene-d$_8$, was reacted with the ligand en (3 μL, 0.05 mmol, 1.1 equiv). After heating the mixture at 90° C. for 3 h, the sample was dried. The residue was dissolved in CD$_2$Cl$_2$ and characterized by NMR. The sample was then dried under low pressure. Yield: 30.3 mg (88%). Anal. Calcd (%) for C$_{41}$H$_{42}$FeN$_2$O$_5$P$_2$Ru:C, 57.15; H, 4.91; N, 3.25 Found: C, 57.10; H, 4.50; N, 2.91. $^1$H NMR (200 MHz, CD$_2$Cl$_2$) δ 7.94-7.20 (m, 20H), 4.67-4.04 (m, 8H), 3.08-2.46 (m, 8H), 1.78 (s broad, 6H). $^{13}$C NMR (50 MHz, CD$_2$Cl$_2$) δ 203.18 (t, J=15.1 Hz), 181.34 (s), 176.62 (dd, J=12.1, 5.5 Hz), 134.53 (t, J=5.2 Hz), 134.01 (t, J=5.3 Hz), 132.99 (dd, J=16.2, 13.5 Hz), 131.31 (s), 129.15 (t, J=4.9 Hz), 128.57 (t, J=4.9 Hz), 79.63 (dd, J=65.8, 9.6 Hz), 75.90 (t, J=4.2 Hz), 75.53 (t, J=4.5 Hz), 73.09 (t, J=3.1 Hz), 72.80 (t, J=3.1 Hz), 45.70 (s), 26.06 (s). $^{31}$P NMR (81.0 MHz, CD$_2$Cl$_2$) δ 40.1. IR (cm$^{-1}$): 1963, 1617, 1569.

Example 11: Synthesis of the Complex [Ru(OAc)(CO)(ampy)(dppf)]OAc (13)

In an NMR tube the complex Ru(OAc)$_2$(CO)(dppf) (33) (30.4 mg, 0.04 mmol, 1 equiv) suspended in 0.6 mL of toluene-d$_8$, was reacted with the ligand ampy (4 μL, 0.04 mmol, 1 equiv). After stirring at room temperature for 2 h, the sample was characterized by NMR. The sample was then dried under low pressure. Yield: 30.1 mg (87%). Anal. Calcd (%) for C$_{45}$H$_{42}$FeN$_2$O$_5$P$_2$Ru:C, 59.41; H, 4.65; N, 3.08 Found: C, 59.10; H, 4.40; N, 2.70. $^1$H NMR (200 MHz, toluene-d$_8$) δ 8.68 (t, J=8.5 Hz, 2H), 8.25-8.10 (m, 2H), 7.99 (t, J=8.1 Hz, 2H), 7.75 (t, J=8.5 Hz, 2H), 7.40-7.24 (m, 2H), 7.16-6.83 (m, 15H), 6.64-6.43 (m, 3H), 6.15-5.92 (m, 1H), 5.80 (s, 1H), 4.71 (s, 1H), 4.21 (s, 1H), 3.91 (s, 1H), 3.72 (s, 1H), 3.48 (s, 1H), 2.54 (t, J=14.6 Hz, 1H), 2.41-2.25 (m, 1H), 1.84 (s, 3H), 1.66 (s, 3H). $^{13}$C NMR (50 MHz, toluene-d$_8$) δ 210.1 (d, J=17.6 Hz), 178.3, 177.0 (d, J=2.8 Hz), 160.1 (d, J=3.9 Hz), 149.1, 136.0 (d, J=11.8 Hz), 135.5, 134.5 (d, J=10.7 Hz), 133.2 (d, J=9.9 Hz), 130.9, 130.0 (d, J=17.4 Hz), 128.3, 127.3, 121.3 (d, J=15.4 Hz), 77.0 (d, J=3.8 Hz), 76.5 (d, J=7.1 Hz), 75.3 (d, J=7.3 Hz), 75.0 (d, J=5.4 Hz), 74.8, 71.3 (d, J=5.3 Hz), 71.1 (d, J=3.5 Hz), 70.3 (d, J=5.8 Hz), 50.4, 26.1, 24.6 (d, J=5.8 Hz). $^{31}$P NMR (81.0 MHz, toluene-d$_8$) δ 51.2 (d, J=29.1 Hz), 40.5 (d, J=29.1 Hz). IR (cm$^{-1}$): 1959, 1609, 1586.

Example 12: Synthesis of the Complex [Ru(OAc)(CO)((R,R)-dpen)(R-Josiphos)]OAc (14)

In an NMR tube the complex Ru(OAc)$_2$(CO)(R-Josiphos) (34) (32.0 mg, 0.04 mmol, 1 equiv) suspended in 0.6 mL of toluene-d$_8$, was reacted with the ligand (R,R)-dpen (8.2 mg, 0.04 mmol, 1 equiv). After stirring at room temperature for 2 h, the sample was characterized by NMR, showing that 2 isomers of the desired product were obtained in a 4/1 ratio. The sample was then dried under low pressure. Yield: 39.1 mg (97%). Anal. Calcd (%) for C$_{55}$H$_{54}$FeN$_2$O$_5$P$_2$Ru:C, 63.40; H, 5.22; N, 2.69; Found: C, 63.00; H, 5.40; N, 2.50. $^{31}$P NMR (81.0 MHz, toluene-d$_8$) δ 60.4 (d, J=35.8 Hz, minor dia), 51.0 (d, J=34.7 Hz, major dia), 41.1 (d, J=34.6 Hz, major dia), 25.7 (d, J=35.8 Hz, minor dia). IR (cm$^{-1}$): 1957, 1601, 1558

Example 13: Synthesis of the Complex [Ru(OAc)(CO)((S,S)-dpen)(R-Josiphos)]OAc (15)

In an NMR tube the complex Ru(OAc)$_2$(CO)(R-Josiphos) (34) (29.9 mg, 0.04 mmol, 1 equiv) suspended in 0.6 mL of toluene-d$_8$, was reacted with the ligand (S,S)-dpen (8.0 mg, 0.04 mmol, 1 equiv). After stirring at room temperature for 2 h, the sample was characterized by NMR, showing that 2 isomers of the desired product was obtained in a 7/3 ratio. The sample was then dried under low pressure. Yield: 36.7 mg (98%). Anal. Calcd (%) for C$_{55}$H$_{54}$FeN$_2$O$_5$P$_2$Ru:C, 63.40; H, 5.22; N, 2.69; Found: C, 63.30; H, 5.50; N, 2.60. $^{31}$P NMR (81.0 MHz, toluene-d$_8$) δ 53.8 (d, J=36.0 Hz, minor dia), 52.6 (d, J=34.4 Hz, major dia), 41.9 (d, J=34.5 Hz, major dia), 36.1 (d, J=36.1 Hz, minor dia). IR (cm$^{-1}$): 1956, 1602, 1562.

Example 14: Synthesis of the Complex RuCl$_2$(CO)(Hamtp)(PPh$_3$) (16)

The complex RuCl$_2$(CO)(dmf)(PPh$_3$)$_2$ (282.3 mg, 0.35 mmol, 1 equiv), suspended in 15 mL of CHCl$_3$, was reacted with the ligand HCNN (70.9 mg, 0.36 mmol, 1.1 equiv). The suspension was stirred at 60° C. overnight and the volume was reduced to about 1 mL. The complex was precipitated by addition of 10 mL of n-pentane. The obtained solid was filtered, washed two times with 5 mL of ethyl ether, one time with 5 mL of n-pentane and dried under reduced pressure. Yield: 160.3 mg (69%). Anal. Calcd (%) for C$_{32}$H$_{29}$Cl$_2$N$_2$OPRu:C, 58.19; H, 4.43; N, 4.24; found: C, 58.20, H, 4.40; N, 4. $^1$H NMR (200 MHz, CD$_2$Cl$_2$) δ 7.89-7.07 (m, 22H), 4.50 (t, J=6.1 Hz, 2H), 3.13 (t, J=5.7 Hz, 2H), 2.49 (s, 3H). $^{13}$C NMR (50 MHz, CD$_2$Cl$_2$) δ 200.7 (d, J=21.5 Hz), 165.5, 161.4, 140.4, 139.4, 137.1, 134.1 (d, J=9.6 Hz), 133.2, 132.3, 130.27, 130.2 (d, J=2.4 Hz), 129.3, 128.3 (d, J=10.0 Hz), 126.0 (d, J=2.3 Hz), 119.8 (d, J=1.4 Hz), 66.0, 50.3, 21.6 (d, J=12.2 Hz). $^{31}$P NMR (81 MHz, CD$_2$Cl$_2$) δ 54.5. IR (cm$^{-1}$): 1947.

Example 15: Synthesis of the Complex RuCl$_2$(CO)(Hambq)(PPh$_3$) (17)

The complex RuCl$_2$(CO)(dmf)(PPh$_3$)$_2$ (365 mg, 0.46 mmol, 1 equiv), suspended in 5 mL of n-BuOH, was reacted with the ligand Hambq (208 mg, 1.03 mmol, 2.2 equiv). The suspension was stirred at 130° C. overnight, the solvent was evaporated under reduced pressure and the residue was dissolved in 1 mL of CHCl$_3$. The solution was stirred for 1 hour at room temperature and the complex was precipitated by addition of 10 mL ethyl ether. The solution was filtered, and the solid was washed 2 times with 3 mL of ethyl ether, one time with 3 mL of n-pentane and dried under reduced pressure. Yield: 291 mg (95%). Anal. Calcd (%) for C$_{33}$H$_{27}$Cl$_2$N$_2$OPRu:C, 59.11; H, 4.06; N, 4.18, found: C, 59.20; H, 4.10; N, 4.26. $^1$H NMR (200 MHz, CD$_2$Cl$_2$) δ 8.12-6.87 (m, 23H), 4.36-4.14 (m, 1H), 4.01-3.83 (m, 1H), 3.54-3.28 (m, 1H), 2.68-2.24 (m, 1H). $^{31}$P NMR (81 MHz, CD$_2$Cl$_2$) δ 36.9. IR (cm$^{-1}$): 1920.

Example 16: Synthesis of the Complex RuCl$_2$(CO)(Hambq$^{Ph}$)(PPh$_3$) (18)

The complex RuCl$_2$(CO)(dmf)(PPh$_3$)$_2$ (245 mg, 0.31 mmol, 1 equiv), suspended in 5 mL of n-BuOH, was reacted with the ligand HCl.Hambg$^{Ph}$ (159 mg, 0.50 mmol, 1.6 equiv) and the base n-Bu$_3$N (0.5 mL, 2 mmol, 6.6 equiv). After stirring at 130° C. overnight, the solvent was evaporated under reduced pressure, the residue dissolved in 3 mL of CHCl$_3$ and the base K$_2$CO$_3$ (200 mg, 1.39 mmol, 4.5 equiv) was added. The mixture was stirred for 2 h at room temperature, the mixture was filtered. The volume was reduced to about 1 mL and the complex was precipitated by addition of 10 mL ethyl ether. The solution was filtered, and the solid was washed 2 times with 3 mL of ethyl ether, one time with 3 mL of n-pentane and dried under reduced pressure. Yield: 101 mg (46%). Anal. Calcd (%) for C$_{39}$H$_{31}$Cl$_2$N$_2$OPRu:C, 62.74; H, 4.18; N, 3.75, found: C, 62.66; H, 4.10; N, 3.92. $^1$H NMR (200 MHz, CD$_2$Cl$_2$) δ 9.21-9.13 (m, 1H), 7.95-7.10 (m, 26H), 4.77-4.54 (m, 1H), 4.26-4.00 (m, 1H), 3.84-3.63 (m, 1H), 3.19-2.98 (m, 1H). $^{31}$P NMR (81 MHz, CD$_2$Cl$_2$) δ 36.9. IR (cm$^{-1}$): 1924.

Example 17: Synthesis of the Complex Ru(OAc)$_2$(Hamtp)(CO)(PPh$_3$) (19)

The complex Ru(OAc)$_2$(CO)(PPh$_3$)$_2$ (100.3 mg, 0.13 mmol, 1 equiv), suspended in 5 mL of toluene, was reacted with the ligand Hamtp (26.7 mg, 0.13 mmol, 1 equiv). After stirring at 110° C. for 2 days, the solution was concentrated to V~0.5 mL, and the complex was precipitated by addition of 7 mL of n-pentane. The mixture was filtered and the solid was washed 2 times with 5 mL of n-Heptane, two times with 3 mL of Et$_2$O and dried under reduced pressure. Yield: 37.1 mg (40%). Anal. Calcd (%) for C$_{36}$H$_{35}$N$_2$O$_5$PRu:C, 61.10; H, 4.98; N, 3.96, found: C, 60.90; H, 5.30; N, 3.80. $^1$H NMR (200 MHz, CD$_2$Cl$_2$) δ 8.28-8.02 (m, 1H), 7.79-7.60 (m, 6H), 7.46-7.37 (m, 6H), 7.30-7.17 (m, 6H), 7.10-7.03 (m, 1H), 6.91 (d, J=8.4 Hz, 1H), 6.73-6.58 (m, 1H), 4.41 (dd, J=16.6, 6.5 Hz, 1H), 4.32-4.07 (m, 2H), 3.53-3.30 (m, 1H), 2.14 (s, 3H), 2.07 (s, 3H), 1.20 (s, 3H). $^{31}$P NMR (81 MHz, CD$_2$Cl$_2$) δ 54.4. IR (cm$^{-1}$): 1914, 1597, 1572.

Example 18: Synthesis of the Complex RuCl(amtp)(CO)(PPh$_3$) (20)

The complex RuCl(CNN)(PPh$_3$)$_2$ (251.9 mg, 0.29 mmol, 1 equiv) was suspended in 5 mL of CH$_2$Cl$_2$ and the mixture was stirred under CO atmosphere (1 atm) overnight at room temperature. The solvent was evaporated under reduced pressure and the residue was purified by column chromatography, eluent CH$_2$Cl$_2$/Et$_2$O (9/1 to 1/1). Yield: 173 mg (94%). Anal. Calcd (%) for C$_{32}$H$_{28}$ClN$_2$OPRu:C, 61.59; H, 4.52; N, 4.49. Found: C, 61.74; H, 4.85; N, 4.66. IR (cm$^{-1}$): 1905.

Example 19: Synthesis of the Complex RuCl(ambq)(CO)(PPh$_3$) (21)

The complex RuCl(ambq)(PPh$_3$)$_2$ (226 mg, 0.26 mmol, 1 equiv) was suspended in 5 mL of CH$_2$Cl$_2$, and the mixture was stirred under CO atmosphere (1 atm) overnight at room temperature. The solvent was evaporated under reduced pressure and the residue was purified by column chromatography, eluent CH$_2$Cl$_2$/Et$_2$O (9/1 to 1/1). Yield: 132 mg (80%). Anal. Calcd (%) for C$_{33}$H$_{26}$ClN$_2$OPRu:C, 62.51; H, 4.13; N, 4.42. Found:C, 62.55; H, 4.10; N, 4.37. $^1$H NMR (200 MHz, CD$_2$Cl$_2$) δ 8.06-7.80 (m, 2H), 7.51-6.92 (m, 20H), 4.53 (dd, J=16.9, 6.7 Hz, 1H), 4.13-3.96 (m, 1H), 3.85-3.60 (m, 1H), 2.76 (t, J=8.7 Hz, 1H). $^{13}$C NMR (50 MHz, CD$_2$Cl$_2$) δ 207.9 (d, J=17.5 Hz), 172.2 (d, J=12.8 Hz), 156.1, 150.7, 142.5, 139.8, 135.5, 134.1 (d, J=19.2 Hz), 133.4, 133.0 (d, J=10.2 Hz), 133.0 (s), 130.1 (d, J=2.3 Hz), 129.6, 128.3 (d, J=9.8 Hz), 125.5, 122.4, 119.8, 116.7, 51.5. $^{31}$P NMR (81 MHz, CD$_2$Cl$_2$) δ 58.4. IR (cm$^{-1}$): 1922.

Example 20: Synthesis of the Complex RuCl(ambq$^{Ph}$)(CO)(PPh$_3$) (22)

The complex RuCl(ambq$^{Ph}$)(PPh$_3$)$_2$ (119.8 mg, 0.13 mmol, 1 equiv) was suspended in 5 mL of CH$_2$Cl$_2$ and the mixture stirred under CO atmosphere (1 atm) at room temperature overnight. The solvent was evaporated under reduced pressure and the residue was purified by column chromatography, eluent CH$_2$Cl$_2$/Et$_2$O (9/1 to 1/1). Yield: 76.6 mg (85%). Anal. Calcd (%) for C$_{39}$H$_{30}$ClN$_2$OPRu:C, 65.96; H, 4.26; N, 3.94. Found: C, 66.31; H, 3.33; N, 4.12. $^1$H NMR (200 MHz, CD$_2$Cl$_2$) δ 8.17-6.89 (m, 26H), 4.57 (dd, J=16.9, 6.5 Hz, 1H), 4.14 (dd, J=17.4, 10.0 Hz, 1H), 3.83 (dd, J=17.0, 7.6 Hz, 1H), 2.99 (dd, J=9.1, 7.0 Hz, 1H). $^{13}$C NMR (50 MHz, CD$_2$Cl$_2$) δ 208.0 (d, J=17.4 Hz, CO), 172.6 (d, J=12.8 Hz, Ru—C), 155.8, 150.9, 148.7, 142.7, 139.9, 138.0, 134.0 (d, J=9.1 Hz), 133.1, 132.9, 132.9, 130.0 (d, J=2.4 Hz), 129.9, 129.6, 129.1, 128.8, 128.3 (d, J=9.8 Hz), 123.6, 120.6, 119.6, 117.2, 51.5. $^{31}$P NMR (81 MHz, CD$_2$Cl$_2$) δ 58.8. IR (cm$^{-1}$): 1920.

Example 21: Synthesis of the Complex RuCl[(2-CH$_2$-6-Me-C$_6$H$_3$)PCy$_2$](CO)(en) (23)

In an NMR tube the complex RuCl[(2-CH$_2$-6-Me-C$_6$H$_3$)PCy$_2$](CO)[(2,6-Me$_2$C$_6$H$_3$)PCy$_2$] (25) (15.5 mg, 0.02 mmol, 1 equiv) was dissolved in 0.6 mL of CD$_2$Cl$_2$. The ligand en (3 μL, 0.04 mmol, 2 equiv) was added. The solution was heated at 50° C. for two days. The $^{31}$P NMR analysis of the tube showed the displacement of one ligand PCy$_2$(Xylyl) and the formation of two isomers of the desired complex 23. $^{31}$P NMR (81 MHz, CD$_2$Cl$_2$) δ 97.4 (s, 1%), 84.5 (s, 35%), 81.1 (s, 23%), 53.1 (s, 5%, OPCy$_2$(Xylyl)), −4.23 (s, 37%, PCy$_2$(Xylyl)).

Example 22: Synthesis of the Complex RuCl[(2-CH$_2$-6-Me-C$_6$H$_3$)PCy$_2$](CO)(ampy) (24)

In an NMR tube the complex RuCl[(2-CH$_2$-6-Me-C$_6$H$_3$)PCy$_2$](CO)[(2,6-Me$_2$C$_6$H$_3$)PCy$_2$] (25) (15.5 mg, 0.02 mmol, 1 equiv) was dissolved in 0.6 mL of CD$_2$Cl$_2$. The ligand en (3 μL, 0.04 mmol, 2 equiv) was added. The solution was heated at 50° C. for two days with formation of complex 24.

Example 23: Synthesis of the Complex RuCl[(2-CH$_2$-6-Me-C$_6$H$_3$)PCy$_2$](CO)[(2,6-Me$_2$C$_6$H$_3$)PCy$_2$] (25)

The complex RuCl$_3$.xH$_2$O (109 mg, 0.43 mmol, 1 equiv), suspended in 4 mL of EtOH, was reacted with the ligand (2,6-Me$_2$C$_6$H$_3$)PCy$_2$ (345 mg, 1.14 mmol, 2.7 equiv) and the base Et$_3$N (250 μL, 1.84 mmol, 4.3 equiv). After stirring at 80° C. for 1 h, formaldehyde (300 μL, 37% solution in water, 3.70 mmol, 8.6 equiv) was added and the mixture was stirred at 80° C. overnight. The volume was reduced to about half and the obtained precipitated was filtered. The solid was washed two times with 2 mL of EtOH, once with 2 mL of Et$_2$O and dried under reduced pressure. Yield: 107 mg (32%). Anal. Calcd (%) for C$_{41}$H$_{61}$ClOP$_2$Ru:C, 64.09; H, 8.00, Found: C, 63.99; H, 8.95. $^1$H NMR (200 MHz, CD$_2$Cl$_2$) δ 7.32-6.86 (m, 6H), 3.78 (d, J=12.9 Hz, 1H), 3.58 (dd, J=15.0, 6.7 Hz, 1H), 2.97-1.11 (m, 53H). $^{13}$C NMR (50 MHz, CD$_2$Cl$_2$) δ 201.6 (dd, J=14.4, 12.1 Hz), 163.7 (dd, J=33.6, 4.2 Hz), 140.8 (d, J=1.4 Hz), 133.8 (d, J=3.0 Hz), 131.3 (d, J=1.4 Hz), 130.9 (d, J=1.7 Hz), 130.5 (d, J=2.5 Hz), 130.1 (d, J=2.1 Hz), 129.8 (d, J=0.9 Hz), 129.5 (d, J=2.4 Hz), 129.1 (d, J=1.1 Hz), 128.9 (d, J=1.3 Hz), 127.7 (d, J=5.5 Hz), 126.0 (d, J=14.4 Hz), 41.7 (d, J=19.2 Hz), 40.6, 39.4 (d, J=13.7 Hz), 39.2 (d, J=8.1 Hz), 35.4 (d, J=13.9 Hz), 33.9 (d, J=25.5 Hz), 32.6 (d, J=5.9 Hz), 31.6 (d, J=4.6 Hz), 30.8 (d, J=10.5 Hz), 30.6 (d, J=3.1 Hz), 30.1 (d, J=4.1 Hz), 29.9, 29.6 (d, J=4.0 Hz), 29.3, 28.8 (d, J=8.5 Hz), 28.5-25.8 (m), 23.7 (d, J=2.2 Hz), 23.2 (t, J=4.0 Hz), 22.7. $^{31}$P NMR (81 MHz, CD$_2$Cl$_2$) δ 67.2 (d, J=281.4 Hz), 40.0 (d, J=281.6 Hz). IR (cm$^{-1}$): 1903.

Example 24: Synthesis of RuCl$_2$(CO)(dppb)(PPh$_3$) (27)

The complex RuCl$_2$(CO)(dmf)(PPh$_3$)$_2$ (100.9 mg, 0.13 mmol, 1 equiv) suspended in 5 mL of CHCl$_3$, was reacted with the ligand dppb (54.6 mg, 0.13 mmol, 1 equiv). After stirring at 60° C. overnight, the solution was concentrated to about 1 mL. The complex was precipitated by addition of 10 mL n-heptane. The obtained solid was filtered, washed 3 times with 4 mL of n-heptane, 3 times with 3 mL of ethyl ether and dried under reduced pressure. Yield: 112.4 mg (75%). Anal. Calcd (%) for C$_{47}$H$_{43}$Cl$_2$OP$_3$Ru:C, 63.52; H, 4.88 Found: C, 64.93; H, 5.99. $^1$H NMR (200 MHz, CDCl$_3$) δ 7.85-7.70 (m, 4H), 7.66-6.97 (m, 28H), 6.89-6.69 (m, 3H), 3.15-2.95 (m, 1H), 2.72-2.40 (m, 3H), 2.34-2.16 (m, 2H), 1.77-1.52 (m, 2H). $^{31}$P NMR (81 MHz, CD$_2$Cl$_2$) δ 27.5 (t, J=25.8 Hz, 1 P), 16.4-14.8 (m, 2P). IR (cm$^{-1}$): 1954.

Example 25: Synthesis of RuCl$_2$(CO)(dppf) (28)

The complex RuCl$_2$(CO)(dmf)(PPh$_3$)$_2$ (199.3 mg, 0.25 mmol, 1 equiv) suspended in 5 mL of toluene, was reacted with the ligand dppf (141.3 mg, 0.25 mmol, 1 equiv). After stirring the mixture at 110° C. for 2 h, the obtained solution was concentrated to about 1 mL, 10 mL n-heptane were added and the suspension was stirred at room temperature for 1 h. The precipitate was filtered, the obtained solid was washed 3 times with 4 mL of n-heptane, 3 times with 3 mL of ethyl ether and dried under reduced pressure. Yield: 99.5 mg (39%). Anal. Calcd (%) for C$_{35}$H$_{28}$Cl$_2$FeOP$_2$Ru:C, 55.73; H, 3.74 Found: C, 55.41; H, 3.33. $^{31}$P NMR (81 MHz, CD$_2$Cl$_2$) δ 53.6 (d, J=27.2 Hz), 46.6 (d, J=26.8 Hz). IR (cm$^{-1}$): 1979.

Example 26: Synthesis of RuCl$_2$(CO)((R)-Josiphos)(PPh$_3$) (29)

The complex RuCl$_2$(CO)(dmf)(PPh$_3$)$_2$ (300.0 mg, 0.38 mmol, 1 equiv) suspended in 5 mL of toluene, was reacted with the ligand (R)-Josiphos (225.2 mg, 0.39 mmol, 1 equiv). After stirring the mixture at 110° C. 2 h, the obtained solution was concentrated to about 1 mL. The complex was precipitated by addition of 10 mL n-heptane, filtered, washed 3 times with 4 mL of n-heptane, 3 times with 3 mL of ethyl ether and dried under reduced pressure. Yield: 345.8 mg. Anal. Calcd (%) for C$_{55}$H$_{47}$Cl$_2$FeOP$_3$Ru:C, 63.23; H, 4.53; Found: C, 62.90; H, 4.20. $^{31}$P NMR (81 MHz, CD$_2$Cl$_2$) δ 47.5 (t, J=22.9 Hz), 13.6 (d, J=22.7 Hz). IR (cm$^{-1}$): 1979.

Example 27: Synthesis of RuCl$_2$(CO)((R)-BINAP)(PPh$_3$) (30)

The complex RuCl$_2$(CO)(dmf)(PPh$_3$)$_2$ (299.7 mg, 0.38 mmol, 1 equiv) suspended in 5 mL of toluene, was reacted with the ligand (R)-BINAP (239.8 mg, 0.39 mmol, 1 equiv). After stirring at 110° C. 2 h, the obtained solution was concentrated to about 1 mL. The complex was precipitated by addition of 10 mL n-heptane, filtered, washed 3 times with 4 mL of n-heptane, 3 times with 3 mL of ethyl ether and dried under reduced pressure. Yield: 359.7 mg (87%). Anal. Calcd (%) for C$_{63}$H$_{48}$Cl$_2$OP$_3$Ru:C, 69.68; H, 4.37; Found: C, 69.80; H, 4.10. IR (cm$^{-1}$): 1981

Example 28: Synthesis of RuCl$_2$(CO)((R,R)-Skewphos)(PPh$_3$) (31)

The complex RuCl$_2$(CO)(dmf)(PPh$_3$)$_2$ (201.1 mg, 0.26 mmol, 1 equiv) suspended in 5 mL of toluene, was reacted with the ligand (R,R)-Skewphos (113.0 mg, 0.26 mmol, 1 equiv). After stirring at 110° C. 2 h, the solution was concentrated to about 1 mL. The complex was precipitated by addition of 10 mL n-heptane, filtered, washed 3 times with 4 mL of n-heptane, 3 times with 3 mL of ethyl ether and dried under reduced pressure. Yield: 150.5 mg (65%). IR (cm$^{-1}$): 1976.

Example 29: Synthesis of Ru(OAc)$_2$(CO)(dppb) (32)

The complex Ru(OAc)$_2$(CO)(PPh$_3$)$_2$ (300.3 mg, 0.39 mmol, 1 equiv) suspended in 5 mL of CH$_2$Cl$_2$, was reacted with the ligand dppb (167.3 mg, 0.39 mmol, 1 equiv). After stirring the mixture at room temperature overnight, the obtained solution was concentrated to about 0.5 mL. The complex was precipitated by addition of 10 mL n-heptane, filtered, washed 3 times with 4 mL of n-heptane, 3 times with 3 mL of ethyl ether and dried under reduced pressure. Yield: 230.1 mg (88%). Anal. Calcd (%) for C$_{33}$H$_{34}$O$_5$P$_2$Ru: C, 58.84; H, 5.09 Found: C, 58.50; H, 5.10. $^1$H NMR (200 MHz, CDCl$_3$, 25° C.) δ 7.92-7.12 (m, 20H), 2.84 (m, 2H), 2.43 (m, 2H), 1.79 (m, 4H), 1.41 (s, 6H). $^1$H NMR (200 MHz, CDCl$_3$, −70° C.) δ 8.07-7.77 (m, 3H), 7.73-7.19 (m, 15H), 7.15-6.92 (m, 2H), 3.37-2.36 (m, 3H), 2.29-1.38 (m, 5H), 1.34 (s, 3H), 1.14 (s, 3H). $^{13}$C NMR (50 MHz, CD$_2$Cl$_2$, 25° C.) δ 204.6 (broad), 133.77-132.48 (m), 130.80 (d, J=25.6 Hz), 129.07-128.33 (m), 30.40 (s, broad), 29.75 (s, broad), 23.79 (s, broad), 23.53 (s, broad). $^{13}$C NMR (50 MHz, CD$_2$Cl$_2$, −70° C.) δ 204.5 (dd, J=21.6, 15.8 Hz), 202.7 (t, J=16.9 Hz), 189.1, 182.4 (t, J=38.8 Hz), 175.3, 136.8 (d, J=51.5 Hz), 133.4 (d, J=18.8 Hz), 131.8, 131.2-130.5 (m), 130.4 (d, J=8.7 Hz), 129.4 (d, J=17.3 Hz), 129.1-128.5 (m), 128.0 (d, J=8.9 Hz), 127.8 (d, J=9.5 Hz) 29.9 (d, J=35.3 Hz), 27.7 (d, J=33.5 Hz), 25.2, 24.4, 21.9 (d, J=4.3 Hz), 20.5. $^{31}$P NMR (81 MHz, CD$_2$Cl$_2$, 25° C.) 46.7 (broad). $^{31}$P NMR (81 MHz, CD$_2$Cl$_2$, −70° C.) δ 48.0 (d, J=27.1 Hz), 46.3 (d, J=25.9 Hz), 38.7 (s, broad). IR (cm$^{-1}$): 1954, 1945.

Example 30: Synthesis of Ru(OAc)$_2$(CO)(dppf) (33)

The complex Ru(OAc)$_2$(CO)(PPh$_3$)$_2$ (200.5 mg, 0.26 mmol, 1 equiv) suspended in 5 mL of toluene, was reacted with the ligand dppf (167.3 mg, 0.26 mmol, 1 equiv). After stirring at 110° C. for 2 h, the solution was concentrated to about 1 mL and the complex was precipitated by addition of 10 mL n-heptane, filtered, washed 3 times with 4 mL of n-heptane, 3 times with 3 mL of ethyl ether and dried under reduced pressure. Yield: 139.6 mg (67%) determined to be a mixture of 3 isomers in a ratio of 7/2/1 at −70° C., the mixture is interchanging at room temperature. Anal. Calcd (%) for $C_{39}H_{34}FeO_5P_2Ru$:C, 58.44; H, 4.28; Found: C, 58.10; H, 4.60. $^1H$ NMR (200 MHz, $CDCl_3$, 25° C.) δ 7.95-7.14 (m broad, 20H), 4.68-4.24 (m broad, 8H), 1.56 (s broad, 6H). $^{13}C$ NMR (50 MHz, $CD_2Cl_2$, 25° C.) δ 134.9-133.1 (m), 130.7 (d, J=16.0 Hz), 129.1-127.2 (m), 75.5 (d, J=36.2 Hz), 73.1, 72.6, 24.2 (s, broad). $^{13}C$ NMR (50 MHz, $CD_2Cl_2$, −70° C.) δ 203.07 (t, J=16.5 Hz), 182.69 (s), 181.93 (s), 134.64 (dd, J=22.9, 9.9 Hz), 132.95 (d, J=9.7 Hz), 132.24-130.81 (m), 129.84 (s), 127.92-126.43 (m), 78.20-76.66 (m), 75.95 (d, J=5.4 Hz), 75.53-74.02 (m), 72.71 (s), 71.80 (d, J=6.1 Hz), 71.14 (d, J=5.4 Hz), 25.40 (s), 24.47 (d, J=4.8 Hz). $^{31}P$ NMR (81 MHz, $CD_2Cl_2$, 25° C.) δ 50.8 (s broad). $^{31}P$ NMR (81 MHz, $CD_2Cl_2$, −70° C.) δ 53.1 (d, J=27.1 Hz, 10%), 52.0 (d, J=26.7 Hz, 23%), 49.8 (d, J=30.4 Hz), 45.4 (d, J=30.4 Hz, 67%), 43.5 (d, J=26.8 Hz, 10%). IR ($cm^{-1}$): 1974, 1613.

Example 31: Synthesis of $Ru(OAc)_2(CO)((R)$-Josiphos) (34)

The complex $Ru(OAc)_2(CO)(PPh_3)_2$ (300.3 mg, 0.39 mmol, 1 equiv) suspended in 5 mL of toluene, was reacted with the ligand (R)-Josiphos (167.3 mg, 0.40 mmol, 1 equiv). After stirring at 110° C. for 2 h, the homogenous solution, was concentrated to about 1 mL and the complex was precipitated by addition of 10 mL n-heptane, filtered, washed 3 times with 4 mL of n-heptane, 3 times with 3 mL of ethyl ether and dried under reduced pressure, leading to a mixture of two diastereoisomers of the product in a 3/2 ratio. Yield: 273.6 mg (85%). Anal. Calcd (%) for $041H_{38}FeO_5P_2Ru$:C, 59.36; H, 4.62 Found: C, 59.30; H, 4.30. $^1H$ NMR (200 MHz, $CD_2Cl_2$, 25° C.) δ 8.25-7.99 (m, 3H), 7.70-7.07 (m, 31H), 7.05-6.87 (m, 2H), 6.72-6.46 (m, 2H), 4.81 (s, 1H, maj dia), 4.65 (s, 1H min dia), 4.49 (s, 1H), 4.44-4.32 (m, 2H), 4.24-4.00 (m, 2H), 3.91 (s, 3H min dia), 3.76 (s, 5H maj dia), 2.09-1.65 (m, 4H), 1.51-1.25 (m, 8H). $^{31}P$ NMR (81 MHz, $CD_2Cl_2$, 25° C.) δ 67.2 (broad, maj dia), 46.5 (broad, maj dia), 35.9 (broad, min dia), 30.5 (broad, min dia). IR ($cm^{-1}$): 1975, 1950, 1614, 1568.

Example 32: Synthesis of $Ru(OAc)_2(CO)((R)$-BINAP) (35)

The complex $Ru(OAc)_2(CO)(PPh_3)_2$ (300.7 mg, 0.39 mmol, 1 equiv) suspended in 5 mL of toluene, was reacted with the ligand (R)-BINAP (243 mg, 0.39 mmol, 1 equiv). After stirring at 110° C. for 2 h, the solution was concentrated to about 1 mL. The complex was precipitated by addition of 10 mL n-heptane, filtered, washed 3 times with 4 mL of n-heptane, 3 times with 3 mL of ethyl ether and dried under reduced pressure. Yield: 314.1 mg (93%). Anal. Calcd (%) for $C_{49}H_{38}O_5P_2Ru$:C, 67.66; H, 4.40 Found: C, 68.00; H, 4.30. $^1H$ NMR (200 MHz, $CD_2Cl_2$, 25° C.) δ 7.97-7.81 (m, 2H), 7.71-7.27 (m, 20H), 7.24-6.99 (m, 4H), 6.92-6.52 (m, 6H), 1.29 (s, 6H). $^{31}P$ NMR (81 MHz, $CD_2Cl_2$, 25° C.) δ 49.87 (s broad), 43.21 (s broad). IR ($cm^{-1}$): 1968, 1616, 1505.

Example 33: Synthesis of $Ru(OAc)_2(CO)((R,R)$-Skewphos) (36)

The complex $Ru(OAc)_2(CO)(PPh_3)_2$ (200.9 mg, 0.26 mmol, 1 equiv) suspended in 5 mL of toluene, was reacted with the ligand (R,R)-Skewphos (114 mg, 0.26 mmol, 1 equiv). After stirring at 110° C. for 2 h, the solution was concentrated to about 1 mL and the complex was precipitated by addition of 10 mL n-heptane, filtered, washed 3 times with 4 mL of n-heptane, 3 times with 3 mL of $Et_2O$ and dried under reduced pressure. Yield: 127.9 mg (71%). Anal. Calcd (%) for $C_{34}H_{36}O_5P_2Ru$:C, 59.38; H, 5.28 Found: C, 59.20; H, 4.90; N, 4.10. $^1H$ NMR (200 MHz, $CD_2Cl_2$, 25° C.) δ 7.78-7.34 (m, 16H), 7.32-7.08 (m, 4H), 3.28-3.03 (m, 1H), 2.85-2.64 (m, 1H), 2.26-2.06 (m, 1H), 2.00-1.77 (m, 1H), 1.57 (s broad, 6H), 0.95 (ddd, J=19.4, 14.0, 7.1 Hz, 6H). $^{31}P$ NMR (81 MHz, $CD_2Cl_2$, 25° C.) δ 55.0 (s, broad), 50.9 (s, broad). IR (cm−1): 1958, 1568.

Example 34: Synthesis of $RuCl_2(CO)(dppb)(HCN)$ (37)

The complex $RuCl_2(CO)(dmf)(PPh_3)_2$ (159.1 mg, 0.20 mmol, 1 equiv) suspended in 3 mL of $CH_2Cl_2$, was reacted with the ligand dppb (85.3 mg, 0.20 mmol, 1 equiv) and stirred at room temperature for 2 h. The solution was dried under vacuum and 2-propanol (3 ml) and the ligand HCN (0.3 mmol, 33 μl, 1.5 eq.) were sequentially added to the obtained residue and the mixture refluxed for 2.5 h. The solvent was evaporated under reduced pressure and the crude product was treated with n-pentane and refluxed for 0.5 h. The precipitated complex was filtrated, washed 3 times with 4 mL of pentane and dried under reduced pressure. Yield: 92 mg (63%). $^{31}P$ NMR (81 MHz, $CD_2Cl_2$, 25° C.) δ 47.6 (d, J=30.2 Hz), 28.2 (d, J=30.2 Hz).

Example 35: Synthesis of $Ru(OAc)_2(CO)(dppb)(HCN)$ (38)

The complex $Ru(OAc)_2(CO)(PPh_3)_2$ (154.3 mg, 0.20 mmol, 1 equiv) suspended in 3 mL of $CH_2Cl_2$, was reacted with the ligand dppb (85.3 mg, 0.20 mmol, 1 equiv) and stirred at room temperature for 2 h. The solvent was evaporated under reduced pressure and 2-propanol (3 ml) and the ligand HCN (0.3 mmol, 33 μl, 1.5 eq.) were sequentially added and the mixture was refluxed for 2.5 h. The solvent was evaporated under reduced pressure and the crude product was treated with pentane and refluxed for 0.5 h (3×3 ml). The precipitated complex was filtrated and dried under reduced pressure. Yield: 90 mg (58%). $^{31}P$ NMR (81 MHz, $CD_2Cl_2$, 25° C.) δ 45.1 (d, J=29.1 Hz), 34.7 (d, J=29.1 Hz).

Example 36: Synthesis of $Ru(OAc)_2(CO)(PNN)$ (39)

The complex $Ru(OAc)_2(CO)(PPh_3)_2$ (201.2 mg, 0.26 mmol, 1 equiv) suspended in 5 mL of toluene, was reacted with the ligand PNN (101.4 mg, 0.27 mmol, 1 equiv). After stirring at 110° C. for 2 h, the solution was concentrated to about 1 mL. The complex was precipitate by addition of 10 mL n-heptane, filtrated, washed 3 times with 4 mL of n-heptane, 3 times with 3 mL of ethyl ether and dried under reduced pressure. Yield: 142.1 mg (87%). Anal. Calcd (%) for $C_{30}H_{29}N_2O_5PRu$:C, 57.23; H, 4.64; N, 4.45 Found: C, 57.60; H, 4.50; N, 4.10. $^1H$ NMR (200 MHz, $CD_2Cl_2$) δ 9.04-8.92 (m, 1H), 8.36 (s, 1H, N—H), 7.93-7.56 (m, 6H), 7.56-7.32 (m, 6H), 7.32-7.12 (m, 4H), 6.97-6.83 (m, 1H), 4.15-4.07 (m, 2H), 3.82-3.64 (m, 1H), 3.52-3.36 (m, 1H), 1.55 (s, 3H), 1.25 (s, 3H). $^{13}C$ NMR (50 MHz, $CD_2Cl_2$) δ 205.0 (d, J=16.5 Hz), 176.5, 176.2, 168.5 (d, J=5.7 Hz), 161.3, 151.7, 138.3, 137.9, 135.8 (d, J=8.7 Hz), 134.6 (d, J=9.9 Hz), 134.1, 134.1 (d, J=10.3 Hz), 132.6 (d, J=6.3 Hz), 131.5 (d, J=2.1 Hz), 130.8 (d, J=2.6 Hz), 130.7 (d, J=3.6 Hz), 130.0, 129.4, 128.7 (d, J=10.3 Hz), 128.2 (d, J=10.5 Hz), 125.1 (d, J=2.8 Hz), 122.8 (d, J=2.3 Hz), 63.5, 37.2, 24.4, 23.6. 31P NMR (81 MHz, $CD_2Cl_2$) δ 49.0. IR (cm−1): 1940, 1626, 1607.

Example 37: Catalytic Reduction by Transfer Hydrogenation of Ketones and Aldehydes with Complexes of Examples 1-39

The catalyst solution was prepared in a 10 mL Schlenk by adding 5 mL of 2-propanol to the chosen ruthenium complex (0.02 mmol). By stirring, the complex dissolved over a period of a few minutes. Separately, in a second Schlenk (20 mL), 250 µL of the previously prepared solution containing the catalyst and 200 µL of a 0.1 M sodium iso-propoxide solution in 2-propanol were added successively to a ketone or aldehyde solution (1 mmol) in 10 mL of 2-propanol under reflux (S/C=1000, S/B=50).

For the reactions, in which the catalyst was formed in situ, a pre-catalyst solution was prepared by adding 5 mL of 2-propanol to the pre-catalyst (0.02 mmol) and the corresponding ligand (0.1 mmol) (see Tables 2 and 3) and the solution was stirred for 30 min at reflux. The solution of the in situ formed catalyst was used in the reduction reaction as described above (S/C=1000, L/C=5, S/B=50).

The start of the reaction was considered to be when the base was added. The molar ratio of substrate/catalyst (S/C) varied from 1000/1 to 50000/1 while the molar ratio substrate/base was in the range of 10/1 to 100/1.

The reaction temperature was kept at 82° C.

The results of the GC analysis for the reduction of acetophenone are reported in Table 2, while those for other ketones and aldehydes are shown in Table 3.

TABLE 2

Catalytic transfer hydrogenation of acetophenone (0.1M) to 1-phenylethanol with the complexes 1-39 and NaOiPr or $K_2CO_3$ as base

| Complex | S/C | Ligand | Base (S/B) | Conversion % (min) | TOF $(h^{-1})^a$ | ee (%) |
|---|---|---|---|---|---|---|
| 1 | 1000 | — | NaOiPr (50/1) | 54 (90) | — | |
| 2 | 1000 | — | NaOiPr (50/1) | 42 (60) | — | |
| 3 | 1000 | — | NaOiPr (50/1) | 27 (90) | | |
| 4 + 5 | 1000 | — | NaOiPr (50/1) | 81 (90) | | |
| 6 + 7 | 1000 | — | NaOiPr (50/1) | 95 (90) | | |
| 8 | 1000 | — | NaOiPr (50/1) | 90 (90) | | |
| 9 | 1000 | — | NaOiPr (50/1) | 88 (90) | | |
| 16 | 1000 | — | NaOiPr (50/1) | 100 (2) | 12000 | |
| 16 | 10000 | — | NaOiPr (50/1) | 100 (36) | 8000 | |
| 18 | 10000 | — | NaOiPr (50/1) | 100 (17) | 20000 | |
| 20 | 10000 | — | NaOiPr (50/1) | 100 (0.06) | 86000 | |
| 20 | 50000 | — | NaOiPr (50/1) | 100 (0.45) | 55000 | |
| 21 | 1000 | — | $K_2CO_3$ (20/1) | 95 (30) | | |
| 21 | 1000 | — | NaOiPr (50/1) | 96 (15) | | |
| 22 | 10000 | — | NaOiPr (50/1) | 100 (17) | 18000 | |
| 27 | 1000 | en | NaOiPr (50/1) | 25 (120) | — | |
| 27 | 1000 | ampy | NaOiPr (50/1) | 38 (120) | — | |
| 28 | 1000 | en | NaOiPr (50/1) | 44 (120) | — | |
| 28 | 1000 | ampy | NaOiPr (50/1) | 90 (120) | 3500 | |
| 29 | 1000 | en | NaOiPr (50/1) | 74 (120) | 400 | 13 |
| 29 | 1000 | ampy | NaOiPr (50/1) | 95 (120) | 1700 | 17 |
| 29 | 1000 | (±)iPr-ampy | NaOiPr (50/1) | 97 (30) | 6700 | 17 |
| 29 | 1000 | (R,R)-DPEN | NaOiPr (50/1) | 96 (120) | 1200 | 59 |
| 29 | 1000 | (S,S)-DPEN | NaOiPr (50/1) | 94 (120) | 700 | 32 |
| 30 | 1000 | en | NaOiPr (50/1) | 92 (120) | 900 | 22 |
| 30 | 1000 | ampy | NaOiPr (50/1) | 88 (300) | 300 | 18 |
| 30 | 1000 | (±)iPr-ampy | NaOiPr (50/1) | 97 (120) | 1200 | 25 |
| 30 | 1000 | (R,R)-DPEN | NaOiPr (50/1) | 93 (120) | 8400 | 32 |
| 30 | 1000 | (S,S)-DPEN | NaOiPr (50/1) | 78 (120) | 1100 | 16 |
| 31 | 1000 | en | NaOiPr (50/1) | 48 (120) | — | 13 |
| 31 | 1000 | ampy | NaOiPr (50/1) | 86 (120) | 1800 | 66 |
| 31 | 1000 | (±)iPr-ampy | NaOiPr (50/1) | 95 (30) | 5800 | 67 |
| 31 | 1000 | (R,R)-DPEN | NaOiPr (50/1) | 85 (120) | 800 | 46 |
| 31 | 1000 | (S,S)-DPEN | NaOiPr (50/1) | 46 (120) | 300 | 53 |
| 32 | 1000 | en | NaOiPr (50/1) | 85 (120) | 3700 | |
| 32 | 1000 | ampy | NaOiPr (50/1) | 93 (120) | 7400 | |
| 33 | 1000 | en | NaOiPr (50/1) | 46 (120) | — | |
| 33 | 1000 | ampy | NaOiPr (50/1) | 72 (120) | 6850 | |
| 34 | 1000 | en | NaOiPr (50/1) | 91 (120) | 1200 | 9 |
| 34 | 1000 | ampy | NaOiPr (50/1) | 94 (30) | 10650 | 2 |
| 34 | 1000 | (±)iPr-ampy | NaOiPr (50/1) | 94 (5) | 16000 | 22 |
| 34 | 1000 | (R,R)-DPEN | NaOiPr (50/1) | 96 (30) | 16000 | 23 |
| 34 | 1000 | (S,S)-DPEN | NaOiPr (50/1) | 96 (30) | 16000 | 1 |
| 35 | 1000 | en | NaOiPr (50/1) | 97 (30) | 6000 | 18 |
| 35 | 1000 | ampy | NaOiPr (50/1) | 94 (5) | 16800 | 23 |
| 35 | 1000 | (±)iPr-ampy | NaOiPr (50/1) | 97 (5) | 19200 | 24 |
| 35 | 1000 | (R,R)-DPEN | NaOiPr (50/1) | 97 (5) | 15000 | 30 |
| 35 | 1000 | (S,S)-DPEN | NaOiPr (50/1) | 96 (5) | 12000 | 19 |
| 36 | 1000 | en | NaOiPr (50/1) | 91 (30) | 10100 | 25 |
| 36 | 1000 | ampy | NaOiPr (50/1) | 95 (30) | 10100 | 25 |
| 36 | 1000 | (±)iPr-ampy | NaOiPr (50/1) | 90 (5) | 15100 | 39 |

TABLE 2-continued

Catalytic transfer hydrogenation of acetophenone (0.1M) to 1-phenylethanol with the complexes 1-39 and NaOiPr or $K_2CO_3$ as base

| Complex | S/C | Ligand | Base (S/B) | Conversion % (min) | TOF $(h^{-1})^a$ | ee (%) |
|---|---|---|---|---|---|---|
| 36 | 1000 | (R,R)-DPEN | NaOiPr (50/1) | 97 (30) | 17700 | 12 |
| 36 | 1000 | (S,S)-DPEN | NaOiPr (50/1) | 92 (30) | 15200 | 26 |
| 39 | 1000 | — | NaOiPr (50/1) | 96 (30) | 13900 | — |

$^a$TOF = turnover frequency (moles of carbonyl compound converted to alcohol per mole of catalyst per hour) at 50% conversion.

TABLE 3

Catalytic transfer hydrogenation of ketones and aldehydes (0.1M) to alcohols with the complexes 1-21 using a ratio substrate/base (NaOiPr) of 50/1

| Complex | Substrate | S/C | Conversion % (min) |
|---|---|---|---|
| 1 | benzaldehyde | 1000 | 11 (10) |
| 3 | benzaldehyde | 1000 | 10 (10) |
| 4 + 5 | benzaldehyde | 1000 | 8 (30) |
| 6 + 7 | benzophenone | 1000 | 92 (10); 94 (30) |
| 6 + 7 | benzaldehyde | 1000 | 14 (60) |
| 6 + 7 | 4-bromobenzaldehyde | 1000 | 30 (60) |
| 8 | benzaldehyde | 1000 | 25 (60) |
| 9 | benzaldehyde | 1000 | 20 (60) |
| 20 | 4-bromobenzaldehyde | 1000 | 97 (10) |
| 20 | (E)-2-methyl-3-phenylacrylaldehyde | 1000 | 93 (40) |
| 21 | benzophenone | 1000 | 94 (30) |
| 21 | benzaldehyde | 1000 | 98 (60) |

Example 38: Catalytic Reduction of Ketones with Complexes of Examples 1-36 Using Molecular Hydrogen The hydrogenation reactions were performed in an 8 vessels Endeavor Parr apparatus. The vessels were charge with the catalysts (2.5 µmol). The vessels were closed, charged with 5 bar of $N_2$ and slowly vented five times. The ketone (5 mmol), optionally ligand (5 µmol), the solvent (0.9 mL) and 1 mL of a solution of t-BuOK 0.1 M were added. The vessels were charged with 20 bar of $H_2$ and slowly vented four times. The vessel was charged to 30 bars and heated to 70° C. (S/C=2000, S/B=50, L/C=2).

The molar ratio of substrate/catalyst varied from 2000/1 to 25000/1 while the molar substrate/base ratio range from 10/1 to 100/1.

The hydrogen uptake was calculated by the apparatus and the results of the GC analysis at the end of the runs are shown in Tables 4 for the catalytic reduction of acetophenone and in Table 5 for other substrates.

For the in situ reactions, the vessel was charge with the precursor catalyst (2.5 µmol) and the corresponding ligand (5 µmol) (L/C=2/1) (see Tables 4 and 5)

TABLE 4

Catalytic hydrogenation (30 bar) of acetophenone to 1-phenylethanol in the presence of the complexes 1-25 using t-BuOK or KOH as base

| Complex | S/C | ligand | solvent | Base (S/B) | conversion % (h) |
|---|---|---|---|---|---|
| 1 | 2000 | — | EtOH | t-BuOK (50/1) | 100 (16) |
| 2 | 2000 | — | EtOH | t-BuOK (50/1) | 100 (16) |
| 3 | 2000 | — | EtOH | t-BuOK (50/1) | 100 (16) |
| 8 | 2000 | — | EtOH | t-BuOK (50/1) | 100 (16) |
| 16 | 2000 | — | MeOH | t-BuOK (20/1) | 63 (16) |
| 17 | 2000 | — | MeOH | t-BuOK (20/1) | 100 (16) |
| 20 | 2000 | — | EtOH | t-BuOK (50/1) | 61 (16) |
| 20 | 2000 | — | MeOH | t-BuOK (20/1) | 25 (16) |
| 21 | 2000 | — | EtOH | t-BuOK (50/1) | 43 (16) |
| 21 | 2000 | — | MeOH | t-BuOK (20/1) | 13 (16) |
| 22 | 2000 | — | EtOH | t-BuOK (50/1) | 42 (16) |
| 22 | 2000 | — | MeOH | t-BuOK (50/1) | 36 (16) |
| 25 | 2000 | — | EtOH | t-BuOK (50/1) | 72 (16) |
| 25 | 2000 | en | EtOH | t-BuOK (50/1) | 100 (16) |
| 25 | 2000 | ampy | EtOH | t-BuOK (50/1) | 100 (16) |
| 25 | 10000 | en | EtOH | t-BuOK (50/1) | 100 (16) |
| 25 | 10000 | ampy | EtOH | t-BuOK (50/1) | 92 (16) |
| 25 | 10000 | en | MeOH | t-BuOK (50/1) | 28 (16) |
| 25 | 10000 | ampy | MeOH | t-BuOK (50/1) | 81 (16) |
| 25 | 10000 | en | MeOH | KOH (50/1) | 27 (16) |
| 25 | 10000 | ampy | MeOH | KOH (50/1) | 91 (16) |
| 25 | 25000 | en | MeOH | KOH (50/1) | 15 (16) |
| 25 | 25000 | ampy | MeOH | KOH (50/1) | 45 (16) |

TABLE 5

Catalytic hydrogenation (30 bar) of ketones to alcohols in the presence of the complexes 1-25 in ethanol using a ratio substrate/t-BuOK of 50/1

| Complex | Ketone | S/C | Ligand | Conversion % (h) |
|---|---|---|---|---|
| 2 | tetralone | 10000 | | 8 (16) |
| 2 | 2'-Me-acetophenone | 10000 | | 100 (16) |
| 2 | 4'-MeO-acetophenone | 500 | | 100 (3) |
| 2 | 4'-$NO_2$-acetophenone | 10000 | | 10 (16) |
| 2 | benzophenone | 500 | | 100 (3) |
| 2 | benzoin | 10000 | | 5 (16) |
| 2 | 2'-Cl-acetophenone | 10000 | | 100 (16) |

TABLE 5-continued

Catalytic hydrogenation (30 bar) of ketones to alcohols in the presence of the complexes 1-25 in ethanol using a ratio substrate/t-BuOK of 50/1

| Complex | Ketone | S/C | Ligand | Conversion % (h) |
|---|---|---|---|---|
| 8 | tetralone | 10000 | | 4 (16) |
| 8 | 2'-Me-acetophenone | 10000 | | 28 (16) |
| 8 | 4'-MeO-acetophenone | 500 | | 75 (3) |
| 8 | 4'-NO$_2$-acetophenone | 10000 | | 1 (16) |
| 8 | benzophenone | 500 | | 100 (3) |
| 8 | benzoin | 10000 | | 9 (16) |
| 8 | 2'-Cl-acetophenone | 110000 | | 100 (16) |
| 16 | tetralone | 10000 | | 2 (16) |
| 16 | 2'-Me-acetophenone | 110000 | | 76 (16) |
| 16 | 4'-MeO-acetophenone | 500 | | 76 (3) |
| 16 | 4'-NO$_2$-acetophenone | 10000 | | 5 (16) |
| 16 | benzophenone | 500 | | 99 (3) |
| 16 | benzoin | 10000 | | 7 (16) |
| 16 | 2'-Cl-acetophenone | 10000 | | 84 (16) |
| 25 | 2-octanone | 1000 | ampy | 36 (3) |
| 25 | isobutyrophenone | 1000 | ampy | 61 (3) |
| 25 | tetralone | 10000 | ampy | 7 (16) |
| 25 | tetralone | 10000 | en | 3 (16) |
| 25 | 2'-Me-acetophenone | 10000 | ampy | 38 (16) |
| 25 | 2'-Me-acetophenone | 10000 | en | 100 (16) |

What is claimed is:

1. A pentacoordinate or hexacoordinate complex of formula (XIV):

MXY(CO)(PNN)   (XIV)

wherein:

M is Ru or Os;

X and Y are, independently, a halide, hydride, C1-C20 carboxylate or C1-C20 alkoxide;

and PNN is a compound of formula (V)

wherein

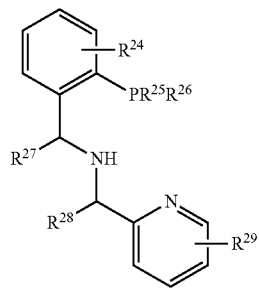

(V)

$R^{21}$-$R^{29}$ are, independently, H, C1-C20 aliphatic group or C5-C20 aromatic group.

2. The complex according to claim 1, wherein X and Y are equal and are Cl, H, C1-C20 alkoxide or C1-C20 carboxylate group.

3. A process for preparing a complex of formula (XIV) of claim 1 comprising reacting a compound of formula MXY(CO)(PPh$_3$)$_2$, or of formula MXY(CO)(PPh$_3$)$_2$(dmf), wherein (dmf) is dimethylformamide, with a tridentate (PNN) ligand of formula (V)

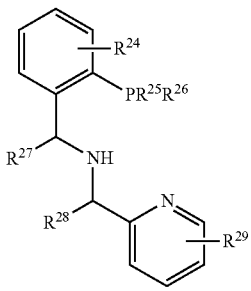

(V)

wherein $R^{24}$-$R^{29}$ are, independently, H, C1-C20 alkyl group or C5-C20 aryl group.

4. A process for reducing a ketone or aldehyde to an alcohol, comprising reducing the ketone or aldehyde using the pentacoordinate or hexacoordinate complex of formula (XIV) of claim 1 as catalyst by transfer hydrogenation or hydrogenation with molecular hydrogen.

5. The process of claim 4, comprising the following steps:

(a) mixing the pentacoordinate or hexacoordinate complex of formula (XIV) with a solution comprising at least one base and at least one substrate selected from the group consisting of C3-C42 ketone and C2-C41 aldehyde thereby obtaining a mixture; and (b) contacting said mixture with molecular H$_2$ or with at least one hydrogen-donor.

6. The process according to claim 4, comprising the following steps:

(a) mixing a pre-catalyst of general formula (2) with a solution comprising at least one base and at least one substrate selected from the group consisting of C3-C42 ketone and C2-C41 aldehyde thereby obtaining a mixture; and (b) contacting said mixture with molecular H$_2$ or with at least one hydrogen-donor, wherein said pre-catalyst has general formula (2):

[MXY$_a$(CO)L'$_c$]W$_d$   (2)

wherein

M is Ru or Os;

a, b and d are independently 0 or 1;

c is 1 or 2;

X and Y are, independently, halide, hydride, C1-C20 carboxylate or C1-C20 alkoxide;

W is halide, C1-C20 carboxylate or C1-C20 alkoxides;

L' is at least one phosphorus-containing ligand that is:

a phosphine (P) that is: a phosphine of formula PR$^{16}$R$^{17}$R$^{18}$, wherein R$^{16}$-R$^{18}$ are, independently, H, C1-C20 aliphatic group or C5-C20 aromatic group; or an optically active phosphine that is (S)-neomenthyldiphenylphosphine or (R)-(+)-2-(diphenylphosphino)-2'-methoxy-1,1'-binaphthyl;

and wherein step (a) is carried out by mixing said pre-catalyst with a solution further comprising at least one nitrogen-containing compound L which is a PNN compound of formula (V)

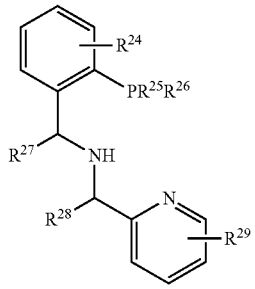

(V)

wherein
$R^{24}$-$R^{29}$ are, independently, H, C1-C20 aliphatic group or C5-C20 aromatic group, and forming the pentacoordinate or hexacoordinate complex of formula (XIV).

7. The process according to claim 5, wherein in step (a) the base is potassium hydroxide, potassium carbonate or an alkali metal alkoxide; and in step (b) the mixture is contacted with molecular hydrogen; or in step (a), the base is sodium iso-propoxide; and in step (b), the mixture is contacted with at least one hydrogen donor.

8. The process according to claim 5, wherein the molar ratio substrate/catalyst or pre-catalyst ranges from 1000/1 to 100000/1 or from 10/1 to 100/1.

9. A process for the reduction of a carbonyl compound by transfer hydrogenation or hydrogenation with molecular hydrogen, the process comprising the use of the pentacoordinate or hexacoordinate complex of formula (XIV) according to claim 1.

* * * * *